US 10,650,920 B2
May 12, 2020

(12) United States Patent
Moturu et al.

(10) Patent No.: US 10,650,920 B2
(45) Date of Patent: May 12, 2020

(54) METHOD AND SYSTEM FOR IMPROVING CARE DETERMINATION

(71) Applicant: Ginger.io, Inc., San Francisco, CA (US)

(72) Inventors: Sai Moturu, San Francisco, CA (US); Anmol Madan, San Francisco, CA (US)

(73) Assignee: Ginger.io, Inc., San Francisco, CA (US)

(*) Notice: Subject to any disclaimer, the term of this patent is extended or adjusted under 35 U.S.C. 154(b) by 91 days.

(21) Appl. No.: 15/587,599

(22) Filed: May 5, 2017

(65) Prior Publication Data

US 2017/0235912 A1    Aug. 17, 2017

Related U.S. Application Data

(63) Continuation-in-part of application No. 13/969,349, filed on Aug. 16, 2013, now Pat. No. 9,836,581.

(Continued)

(51) Int. Cl.
*G16H 15/00*     (2018.01)
*G06F 19/00*     (2018.01)

(Continued)

(52) U.S. Cl.
CPC ......... *G16H 15/00* (2018.01); *G06F 19/3418* (2013.01); *G06F 19/3456* (2013.01);

(Continued)

(58) Field of Classification Search
None
See application file for complete search history.

(56) References Cited

U.S. PATENT DOCUMENTS 6,356,940 B1    3/2002   Short
7,188,151 B2    3/2007   Kumar et al.
(Continued)

FOREIGN PATENT DOCUMENTS

CN    101600008       12/2009
JP    2010514497 A    5/2010
(Continued)

OTHER PUBLICATIONS

"European Office Action application No. 13 829 654.6, dated Jun. 11, 2019."

(Continued)

*Primary Examiner* — Michael Tomaszewski
(74) *Attorney, Agent, or Firm* — Jeffrey Schox; Caitlin Ploch

(57) ABSTRACT

Embodiments of a method and system for improving care determination for care providers in relation to a condition of a user associated with a mobile device can include: collecting a log of use dataset associated with user digital communication behavior at the mobile device; collecting a mobility supplementary dataset corresponding to a mobility-related sensor of the mobile device; determining a medical status analysis for a condition of the user based on at least one of the log of use dataset and the mobility supplementary dataset, the medical status analysis including at least one of a diagnosis and a therapeutic intervention associated with the condition; and promoting the at least one of the diagnosis and the therapeutic intervention to a care provider.

20 Claims, 25 Drawing Sheets

Related U.S. Application Data

(60) Provisional application No. 61/683,867, filed on Aug. 16, 2012, provisional application No. 61/683,869, filed on Aug. 16, 2012, provisional application No. 62/332,897, filed on May 6, 2016, provisional application No. 62/359,600, filed on Jul. 7, 2016.

(51) Int. Cl.
*G16H 50/30* (2018.01)
*G16H 50/20* (2018.01)
*G16H 50/50* (2018.01)
*G16H 40/20* (2018.01)
*G16H 40/67* (2018.01)
*G16H 10/20* (2018.01)

(52) U.S. Cl.
CPC ............ *G16H 40/20* (2018.01); *G16H 40/67* (2018.01); *G16H 50/20* (2018.01); *G16H 50/30* (2018.01); *G16H 50/50* (2018.01); *G16H 10/20* (2018.01)

(56) References Cited

U.S. PATENT DOCUMENTS

| | | | |
|---|---|---|---|
| 7,248,677 | B2 | 7/2007 | Randall et al. |
| 7,376,700 | B1 | 5/2008 | Clark et al. |
| 7,584,166 | B2 | 9/2009 | Grichnik |
| 7,761,309 | B2 | 7/2010 | Sacco et al. |
| 7,912,528 | B2 | 3/2011 | Krishnan et al. |
| 8,160,901 | B2 | 4/2012 | Heywood et al. |
| 8,500,635 | B2 | 8/2013 | Zilca et al. |
| 8,655,817 | B2 | 2/2014 | Hasey et al. |
| 8,684,922 | B2 | 4/2014 | Tran |
| 9,195,948 | B2 | 11/2015 | Son et al. |
| 9,294,403 | B2 | 3/2016 | Mejia et al. |
| 9,684,922 | B2 | 6/2017 | Elberbaum |
| 2002/0198473 | A1 | 12/2002 | Kumar et al. |
| 2003/0119794 | A1 | 6/2003 | Bacaner et al. |
| 2004/0078223 | A1 | 4/2004 | Sacco et al. |
| 2004/0143453 | A1* | 7/2004 | Weaver ............... G06Q 30/02 705/2 |
| 2004/0225340 | A1 | 11/2004 | Evans |
| 2005/0020903 | A1 | 1/2005 | Krishnan et al. |
| 2005/0055321 | A1 | 3/2005 | Fratkina et al. |
| 2005/0069936 | A1 | 3/2005 | Diamond et al. |
| 2005/0108051 | A1* | 5/2005 | Weinstein ............ G06Q 50/22 705/2 |
| 2005/0169446 | A1 | 8/2005 | Randall et al. |
| 2006/0064037 | A1 | 3/2006 | Shalon et al. |
| 2007/0226012 | A1 | 9/2007 | Salgado et al. |
| 2007/0288266 | A1* | 12/2007 | Sysko .................. G06Q 10/00 705/2 |
| 2010/0082367 | A1* | 4/2010 | Hains ................. G06F 19/3456 705/2 |
| 2010/0179833 | A1 | 7/2010 | Roizen et al. |
| 2010/0203876 | A1 | 8/2010 | Krishnaswamy |
| 2010/0280838 | A1 | 11/2010 | Bosworth et al. |
| 2011/0009715 | A1 | 1/2011 | O& et al. |
| 2011/0082712 | A1 | 4/2011 | Eberhardt, III et al. |
| 2011/0118555 | A1* | 5/2011 | Dhumne .................. A61B 5/16 600/300 |
| 2011/0119212 | A1 | 5/2011 | De et al. |
| 2011/0184250 | A1 | 7/2011 | Schmidt et al. |
| 2011/0295621 | A1 | 12/2011 | Farooq et al. |
| 2012/0143013 | A1 | 6/2012 | Davis, III et al. |
| 2012/0289791 | A1 | 11/2012 | Jain et al. |
| 2013/0041290 | A1 | 2/2013 | Kording et al. |
| 2013/0042116 | A1 | 2/2013 | Sakumoto |
| 2013/0085758 | A1 | 4/2013 | Csoma et al. |
| 2013/0085773 | A1 | 4/2013 | Yao et al. |
| 2013/0095459 | A1 | 4/2013 | Tran |
| 2013/0117040 | A1 | 5/2013 | James et al. |
| 2013/0154838 | A1 | 6/2013 | Alameh et al. |
| 2013/0179178 | A1 | 7/2013 | Vemireddy et al. |
| 2013/0246330 | A1 | 9/2013 | Son et al. |
| 2013/0297536 | A1* | 11/2013 | Almosni ............... G16H 50/20 706/12 |
| 2013/0324861 | A1 | 12/2013 | Ando et al. |
| 2014/0019161 | A1 | 1/2014 | Op Den Buijs et al. |
| 2014/0039907 | A1* | 2/2014 | Schaefer ............... G06Q 10/06 705/2 |
| 2014/0039914 | A1 | 2/2014 | Dansereau et al. |

FOREIGN PATENT DOCUMENTS

| | | |
|---|---|---|
| JP | 2015514497 A | 5/2015 |
| WO | 085308 | 7/2008 |
| WO | 096634 | 8/2008 |
| WO | 025622 | 3/2012 |
| WO | 003247 | 1/2015 |

OTHER PUBLICATIONS

Thomee, Sara, et al., "Mobile phone use and stress, sleep disturbances, and symptoms of depression among young adults—a prospective short study", BMC Public Health, Biomed Central, London, GB, vol. 11, No. 1, Jan. 31, 2011, p. 66.

Yen, Cheng-Fang, et al., "Symptoms of problematic cellular phone use, functional impairment and its association with depression among adolescents in Southern Taiwan", Journal of Adolescence, Academic Press, Amsterdam, NL, vol. 32, No. 4, Aug. 1, 2009, pp. 863-873.

* cited by examiner

Care Provider (CP)

Care Provider (CP)

Name: Super Sara
Sex: Female
Age: 37

Patient has been working with a Ginger.io Health Coach for 3 MONTHS,
and a Licensed Therapist for 1 MONTH Signs and symptoms may be consistent with[1]
DEPRESSION

| SCREENING | PATIENT-REPORTED DIAGNOSES | PATIENT-REPORTED SYMPTOMS |
|---|---|---|
| 17 Moderately severe Depression (PHQ-9) | None | Depressed Mood Lack of Interest Difficulty Concentrating Difficulty Sleeping |
| 6 Mild Anxiety (GAD-7) | | |
| 1 Negative screen Bipolar Disorder (MDQ) | | Patient indicated having thoughts about self-harm or suicidality (positive response to the 9th question of the PHQ-9) |

Options to consider for a starting medication[2]
Medication name and manufacturer recommended initial adult dosage

ZOLOFT     OR     CELEXA     OR     REMERON
50mg                  20mg                   15mg

| DECISION RESOURCES | Patient-reported data | Consider | Use with caution | Avoid |
|---|---|---|---|---|
| Conditions | Hypertension | Zoloft | SNRIs, Wellbutrin | |
| | Chronic pain | SNRIs | | |
| Behaviors & symptoms | Fatigue or lethargy | Wellbutrin, Zoloft, Prozac | | |
| | Trying to conceive | | Prozac, Paxil | |
| Current medications | Tenormin | | Lexapro | |

Other conditions: Hypothyroidism
Other medications: Metformin, Synthroid

FIGURE 14A

Name: Super Sara
Sex: Female
Age: 37

Patient has been working with a Ginger.io Health Coach for 3 MONTHS, and a Licensed Therapist for 1 MONTH Signs and symptoms may be consistent with[1]
DEPRESSION

| SCREENING | PATIENT-REPORTED DIAGNOSES | PATIENT-REPORTED SYMPTOMS |
|---|---|---|
| 17 Moderately severe<br>Depression (PHQ-9) | None | Manic Symptoms<br>Depressed Mood<br>Lack of Interest<br>Difficulty Concentrating<br>Difficulty Sleeping |
| 6 Mild<br>Anxiety (GAD-7) | | |
| 9 Positive screen<br>Bipolar Disorder (MDQ) | | Patient indicated having thoughts about self-harm or suicidality (positive response to the 9th question of the PHQ-9) |

CONSIDER REFERRING THIS PATIENT TO A PSYCHIATRIST
We are unable to provide medication decision support for a patient with these symptoms.
Please feel free to contact our psychiatrist if you need a consultation:

Dr. Akhil Mehra, M.D.
Board-certified Psychiatrist
1-855-GINGER-IO or hello@ginger.io

FIGURE 14B

| | |
|---|---|
| Name: | Sara Super |
| Sex: | Female |
| Age: | 37 |

Patient has been working with a Ginger.io Health Coach for 3 MONTHS, and a Licensed Therapist for 1 MONTH

Possible Condition¹
DEPRESSION

| Screening | Patient-reported Diagnoses | Patient-reported Symptoms | |
|---|---|---|---|
| Depression (PHQ-9) 17 | None | Severe | Interest Deficit |
| 2 days ago — Moderately severe | | | Concentration Deficit |
| Anxiety (GAD-7) 6 | | Moderate | Suicidality |
| 4 days ago — Mild | | Mild | Sleep Issues |
| | | | Appetite Issues |
| Bipolar (MDQ)ᵃ 1 | | | |
| 2 days ago — Minimal | | | |

ᵃNumber indicates positive symptoms (7 or more out of 13 is required for a positive screen)

Possible Medication²
SERTRALINE (ZOLOFT)

DECISION RESOURCES

| First Medication | Patient-reported behaviors* | Patient-reported medications | |
|---|---|---|---|
| SSRI/SNRI is recommended as first medication for treating depression | Breastfeeding — Lactation rating L2* | Metformin* | No interactions with Zoloft* |
| | | Levothyroxine | No interactions with Zoloft* |

PATIENT-REPORTED MEDICAL HISTORY

| Medical Conditions | | Life Events | | Family History | |
|---|---|---|---|---|---|
| Diabetes Type II* | 6 years | Divorced | 3 months | Mental Illness | None Reported |
| Hypothyroidism | 4 years | Delivered baby | 8 months | Suicide | None Reported |

¹ Fluoxetine (Prozac) may affect blood sugar
² All psychiatric medication can enter breastmilk
* No reported smoking or substance abuse

FIGURE 14C

Name: Super Sara
Sex: Female
Age: 37

Patient has been working with a Ginger.io Health Coach for 4 MONTHS,
and a Licensed Therapist for 2 MONTH Assessment of response to medication[1]
PARTIAL RESPONSE

| PATIENT-REPORTED DATA | | PATIENT-REPORTED RESPONSE | PATIENT-REPORTED SIDE-EFFECTS |
|---|---|---|---|
| Diagnosis | Depression | 19, 16 (PHQ-9 score vs Days since medication use) | Sleep troubles |
| Medications | Zoloft | | Nausea |
| Dosage | 50mg | | |
| Prescribed | Feb 2016 | | |
| Adherence | High | | |

Dosage adjustment options to consider[2]
Medication name and manufacturer recommended maximum adult dosage
ZOLOFT
Upto 200mg

| SIDE-EFFECT REMEDIES | |
|---|---|
| Sleep troubles | Morning dosing, adding melatonin |
| Nausea | Taking medicine after food |

FIGURE 15A

Name: Super Sara
Sex: Female
Age: 37

Patient has been working with a Ginger.io Health Coach for 5 MONTHS, and a Licensed Therapist for 3 MONTH Assessment of response to medication[1]
PARTIAL RESPONSE PATIENT-REPORTED DATA
Diagnosis: Depression
Medications: Zoloft
Dosage: 150mg
Prescribed: Feb 2016
Adherence: High PATIENT-REPORTED RESPONSE
19, 16, 11
PHQ-9 score
Days since starting medication PATIENT-REPORTED SIDE-EFFECTS
Sleep troubles
Dry mouth Options to consider for augmentation to current treatment[2]
Medication name and manufacturer recommended initial adult dosage

CELEXA       OR    # CYTOMEL
50mg                  25mcg

DECISION RESOURCES

|  | Patient-reported data | Consider | Use with caution | Avoid |
|---|---|---|---|---|
| Conditions | Hypertension | Zoloft | SNRIs, Wellbutrin |  |
|  | Chronic pain | SNRIs |  |  |
| Behaviors & symptoms | Fatigue or lethargy | Wellbutrin, Prozac, Cytomel |  |  |
|  | Trying to conceive |  | Prozac, Paxil |  |
| Current medications | Tenormin |  | Lexapro |  |

Other conditions: Hypothyroidism
Other medications: Metformin, Zestril

SIDE-EFFECT REMEDIES

Sleep troubles    Morning dosing, adding melatonin
Dry mouth         Using sugarless gum

FIGURE 15B

Name: Sara Super
Sex: Female
Age: 37

Patient has been working with a Ginger.io Health Coach for 4 MONTHS,
and a Licensed Therapist for 2 MONTHS Patient-reported Response:
SEVERE SIDE EFFECTS Efficacy

Days since prescription

Patient-reported Medications:
Diagnosis: Depression
Medication: Sertraline (Zoloft)
Prescribed: Feb 2016
Adherence: High Patient-reported Side Effects
Severe: Sleep Troubles
       Nausea
Moderate: Dry Mouth Possible Action?
CHANGE MEDICATION TO PAROXETINE (PAXIL)

DECISION RESOURCES
Second Medication  Choosing a different SSRI/SNRI is recommended for severe side effects from first SSRI medication[a]

Possible side effect remedies[a,b]
Sleep problems: Use morning dosing,
                can add melatonin
Nausea:         Take medicine after food
Dry Mouth:      Use sugarless gum Patient-reported behaviors[c]
Breastfeeding  Lactation rating L2[b]

Patient-reported medications
Metformin[a]    No interactions
Levothyroxine   No interactions

PATIENT-REPORTED MEDICAL HISTORY

Medical Conditions
Diabetes Type II[a]   6 years
Hypothyroidism        4 years

Life Events
Divorced         3 months
Delivered baby   8 months

Family History
Mental Illness   None Reported
Suicide          None Reported

[a] Fluoxetine (Prozac) may affect blood sugar
[b] All psychiatric medication can enter breastmilk
[c] No reported smoking or substance abuse

FIGURE 15C

PATIENT-REPORTED DATA

SCREENING and DIAGNOSIS
We gather data from patients using screeners for Major depressive disorder (PHQ-9), Generalized anxiety disorder (GAD-7), Bipolar disorder (MDQ). We also gather data about past psychiatric diagnoses. This information is summarized to enable PCPs move faster through the diagnosis process.

CONDITIONS and MEDICATIONS
We gather data from patients about current conditions that may be relevant to medication decisions. Their answers are then used to infer potential medications. Users pick from the following list:

We ask patients to provide both current and past psychiatric medications. We also ask about other medications to check for interactions with potential psychiatric medications.

BEHAVIORS, SYMPTOMS and SIDE EFFECTS
We gather data from patients about certain behaviors and symptoms that may be relevant to medication decisions. Users pick from the following list:

If the patient is on a psychiatric medication, we also ask about the side effects they are facing. Users pick from a list of common side effects for the medication in question.

MEDICATION DECISION SUPPORT

MEDICATIONS CONSIDERED
We consider medications that are most frequently prescribed by PCPs for depression. We've ensured that there are a variety of options to choose from for most cases. The following medications are considered for this report:

SSRIs:                SNRIs:

Augmentation:

Other:

From this initial list, options are excluded based on patient-reported data and its relevance to the medication choice. If many options remain, we choose a subset that is considered to have a higher likelihood of acceptability and efficacy based on the literature referenced below.

TREATMENT PROTOCOL SUMMARY
A succinct summary of the treatment protocol considered for this report is as follows:

1. Try a medication that is suitable for the patient's situation.
2. If partial response is seen, try increasing dosage, then try an augmentation strategy if necessary.
3. If no response is seen on first medication, switch medication and repeat first two steps.
4. If no response is seen on second medication, refer case to a psychiatrist.

FIGURE 16

↻ Restore

Page 1:

This survey will take 5 minutes to complete and will help us create a useful report for your primary care provider. The report will help your PCP in making the best medication decisions for you. 

1. Enter your full name *This question is required.

2. Enter your doctor's name *This question is required.

3. Enter your doctor's fax number
(This will be used to share the report with your doctor. Please check the number for accuracy.) *This question is required.

4. Select your gender *This question is required.
- ◯ Female
- ◯ Male

☑ This question has answer validation          View Conditions ▾

5. Enter your age *This question is required.

FIGURE 17A

6.
**Have you been ever diagnosed with a mental health condition by a medical provider?
Please select all past diagnoses from the following list.**

*This question is required.

- ☐ Major Depressive Disorder (MDD)
- ☐ Anxiety disorder (Generalized Anxiety Disorder or Panic Disorder or Social Anxiety Disorder)
- ☐ Bipolar disorder
- ☐ Schizophrenia
- ☐ Post-Traumatic Stress Disorder (PTSD)
- ☐ Attention Deficit Hyperactivity Disorder (ADHD)
- ☐ Obsessive Compulsive Disorder (OCD)
- ☐ Borderline Personality Disorder
- ☐ Other - Write In (Required) Please enter an 'other' value for this selection. [_____] *

This question is required.
- ☐ None of the above

---

7. Have you ever been treated with a psychiatric medication? *This question is required.
   - ☐ Yes
   - ☐ No

---

✏ This question has display logic    View Conditions ▼

8. List any psychiatric medications you are CURRENTLY taking

| 8. List any psychiatric medications you are CURRENTLY taking Name | Dosage |
|---|---|
| 1. | |
| 2. | |
| 3. | |
| 4. | |

---

✏ This question has display logic    View Conditions ▼

9. List the side effects you may be facing due to your CURRENT medications
1. [_____]
2. [_____]
3. [_____]

FIGURE 17B

10. During an average week, how often do you miss a dose of your psychiatric medication? *This question is required.
- 1. One day or less
- 2.Two to three days
- 3.Four or more days ✏️ This question has display logic                                    View Conditions ▾

11. List any other psychiatric medications that you have taken IN THE PAST
1.
2.
3.
4.
5.

12. Do you have any of the following medical conditions?
Please select all relevant conditions from the following list. *This question is required.
- Angle Closure Glaucoma
- Cardiac Conditions (such as Coronary artery disease, Congestive heart failure, Myocardial infarction, Cardiac arrest, Arrythmia or Atrial Fibrillation, Stroke)
- Chronic Pain
- Eating disorders (such as Anorexia nervosa, Bulimia nervosa)
- Hepatic or Liver Disease (such as Hepatitis, Cirrhosis)
- Hyperlipidemia (High cholesterol or triglycerides)
- Hypertension (High blood pressure)
- Renal or Kidney Disease
- Seizures
- Urinary Incontinence
- None of the above 13. Do you face any of the following?
- Insomnia (difficulty falling and/or staying asleep)
- Hypersomnia (prolonged nighttime sleep and excessive daytime sleepiness)
- Being overweight or obese
- Being underweight

FIGURE 17C

14. Do you smoke? *This question is required.
- Yes
- No

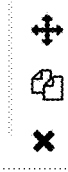

✏️ This question has display logic                    View Conditions ▼

15. Are you interested in quitting smoking? *This question is required.
- Yes
- No

16. If you drink alcohol, have you ever experienced alcohol withdrawal (shakes, delirium), needing a drink to make it go away? *This question is required.
- Yes
- No
- I do not drink alcohol

✏️ This question has display logic                    View Conditions ▼

17. Are you currently pregnant? *This question is required.
- Yes
- No

✏️ This question has display logic                    View Conditions ▼

18. Are you looking to conceive in the next year? *This question is required.
- Yes
- No

19. Please list all medications you are currently taking, including over-the-counter medications, herbals, and supplements.
(Include each medication on a separate line)

FIGURE 17D

20. Has there ever been a period of time when you were not your usual self and... *This question is required.

| 20. Has there ever been a period of time when you were not your usual self and... *This question is required. | Yes | No |
|---|---|---|
| ...you felt so good or so hyper that other people thought you were not your normal self, or you were so hyper that you got into trouble? | | |
| ...you were so irritable that you shouted at people or started fights or arguments? | | |
| ...you felt much more self-confident than usual? | | |
| ...you got much less sleep than usual and found you didn't really miss it? | | |
| ...you were much more talkative or spoke faster than usual? | | |
| ...thoughts raced through your head or you couldn't slow your mind down? | | |
| ...you were so easily distracted by things around you that you had trouble concentrating or staying on track? | | |
| ...you had much more energy than usual? | | |
| ...you were much more active or did many more things than usual? | | |
| ...you were much more social or outgoing than usual; for example, you telephoned friends in the middle of the night? | | |
| ...you were much more interested in sex than usual? | | |
| ...you did things that were unusual for you or that other people might have thought were excessive, foolish, or risky? | | |
| ...spending money got you or your family into trouble? | | |
| If you checked YES to more than one of the above, have several of these ever happened during at least a four day period of time? | | |

21. How much of a *problem* did any of these (from the previous question) cause you -- like being unable to work; having family, money, or legal troubles; getting into arguments or fights? *This question is required.

- ◎ No problem
- ◎ Minor problem
- ◎ Moderate problem
- ◎ Serious problem

FIGURE 17E

METHOD AND SYSTEM FOR IMPROVING CARE DETERMINATION

CROSS-REFERENCE TO RELATED APPLICATIONS

This application is a continuation-in-part of U.S. application Ser. No. 13/969,349 filed 16 Aug. 2013, which claims the benefit of U.S. Provisional Application Ser. No. 61/683,867 filed on 16 Aug. 2012 and U.S. Provisional Application Ser. No. 61/683,869 filed on 16 Aug. 2012, which are each incorporated in its entirety herein by this reference.

This application additionally claims the benefit of U.S. Provisional Application No. 62/359,600 filed 7 Jul. 2016, and U.S. Provisional Application No. 62/332,897 filed 6 May 2016, each of which are incorporated in their entirety by this reference.

TECHNICAL FIELD

This invention relates generally to the digital health field, and more specifically to a new and useful system and method of leveraging patient digital communication behavior to provide decision support for care providers.

BRIEF DESCRIPTION OF THE FIGURES

FIGS. 14A-14C, 15A-15C, and 16 are schematic representations of examples of medical status analyses; and FIGS. 17A-17E are schematic representations of examples of survey questions according to variations of a method.

DESCRIPTION OF THE PREFERRED EMBODIMENTS

Figure 1A:
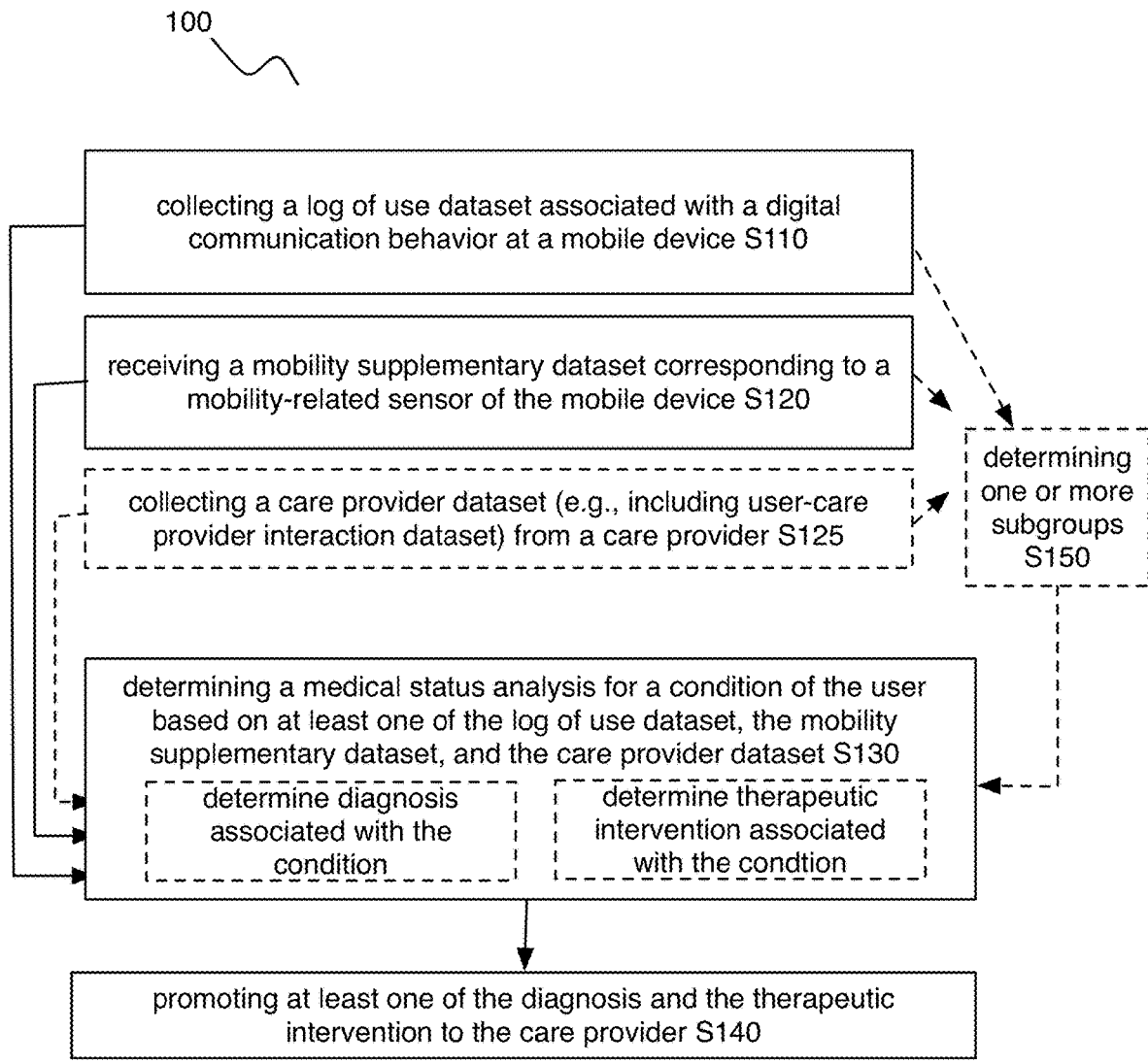
FIGS. 1A-1C are schematic representations of variations of a method for improving care determination.
Figure 1B:
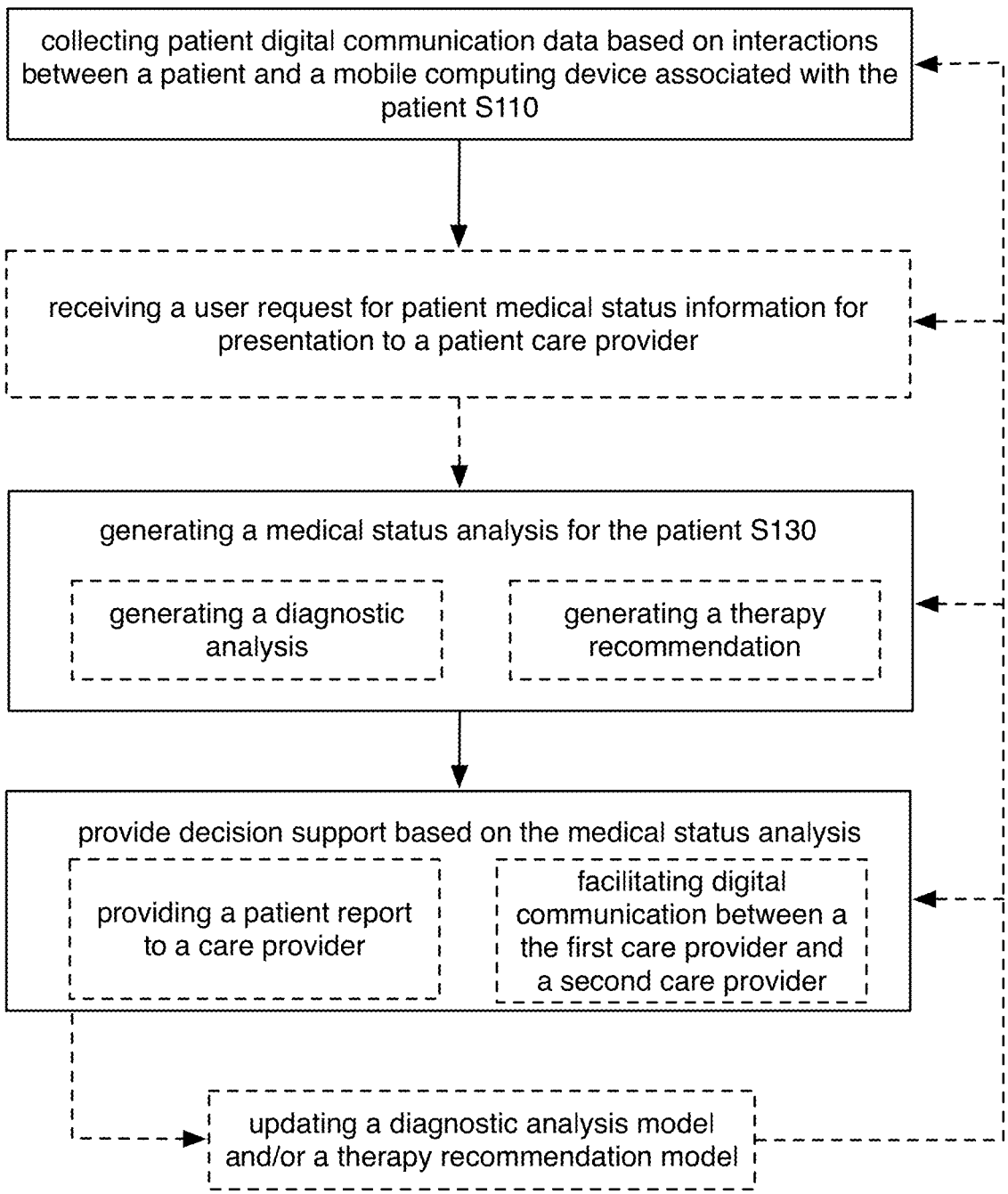
Figure 1C:
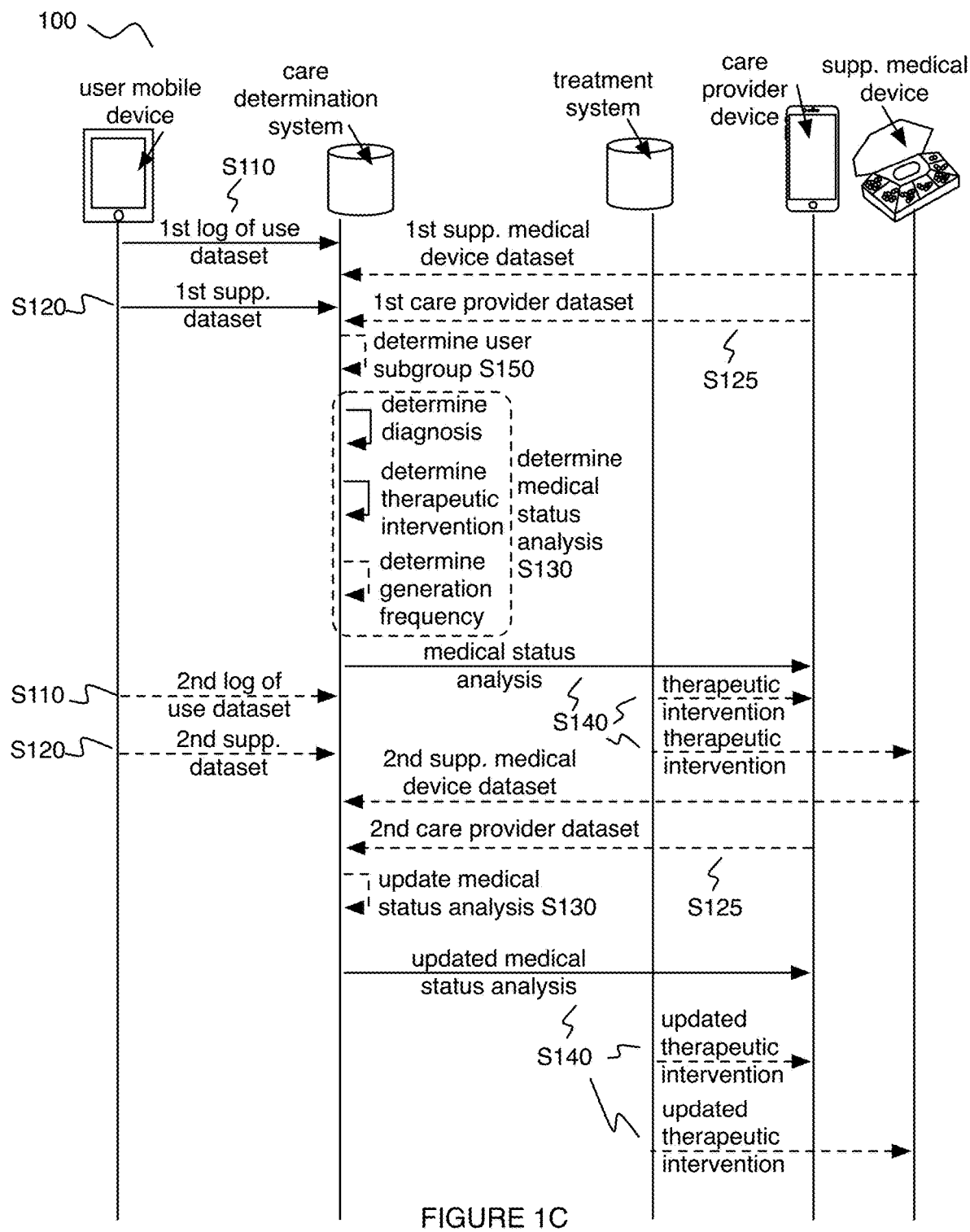

The following description of the preferred embodiments of the invention is not intended to limit the invention to these preferred embodiments, but rather to enable any person skilled in the art to make and use this invention.

1. Overview

As shown in FIGS. 1A-1C and 2-3, embodiments of a method 100 for improving care determination for care providers (e.g., care professionals) in relation to a condition of a user (e.g., patient) associated with a mobile device can include: collecting a log of use dataset associated with user digital communication behavior at the mobile device S110; collecting a mobility supplementary dataset corresponding to a mobility-related sensor of the mobile device S120; determining a medical status analysis for a condition of the user based on at least one of the log of use dataset and the mobility supplementary dataset, the medical status analysis including at least one of a diagnosis and a therapeutic intervention associated with the condition S130; and promoting the at least one of the diagnosis and the therapeutic intervention to a care provider S140. The method 100 can additionally or alternatively include collecting a care provider dataset (e.g., a care professional dataset) from a care provider S125; assigning the user to a user subgroup S150; and/or any other suitable processes.

The method 100 and/or system 200 function to leverage patient digital communication behaviors (e.g., text messaging characteristics, phone calling characteristics, etc.) and/or other behaviors (e.g., mobility behaviors, user-provider interaction behaviors associated with interactions between a user and a care provider, behaviors determined based on user inputs such as survey responses, device event behaviors, etc.) to provide one or more care providers with diagnostic and/or therapeutic intervention information pertaining to the user and/or user condition. As shown in FIGS. 6A-6B, 7-8, and 9A-9B, in variations of the method 100 and/or system 200, tools can be provided to care providers for improving accuracy and confidence in diagnostic and/or therapeutic decisions regarding patient treatment, and/or tools can be provided to patients for increasing treatment information transparency and confidence in a care provider's recommended treatments. A care provider can include a primary care physician, but can additionally or alternatively include a psychiatrist, therapist, heath coach, nurse practitioner, guardian, friend, other healthcare professional and/or any other suitable provider of care for one or more users. In variations, the method 100 and/or system 200 can additionally or alternatively function to support care determination for characterizing and/or improving user conditions including any one or more of: psychiatric and behavioral disorders (e.g., a psychological disorder; depression; anxiety; bipolar disorder; mania; psychosis; associated symptoms; etc.); communication-related conditions (e.g., expressive language disorder; stuttering; phonological disorder; autism disorder; voice conditions; hearing conditions; eye conditions; etc.); sleep-related conditions (e.g., insomnia, sleep apnea; etc.); cardiovascular-related conditions (e.g., coronary artery disease; high blood pressure; hypertension etc.); rheumatoid-related conditions (e.g., arthritis, etc.); pain-related conditions (e.g., chronic pain; etc.); energy-related conditions (e.g., fatigue; lethargy; etc.) endocrine-related conditions; genetic-related conditions; and/or any other suitable type of conditions. User conditions can include at least one of: symptoms, causes, diseases, disorders, side effects (e.g., from medications; etc.), and/or any other suitable aspects associated with conditions.

One or more instances of the method 100 and/or processes described herein can be performed asynchronously (e.g., sequentially), concurrently (e.g., in parallel; concurrently on different threads for parallel computing to improve system processing ability for supporting care providers; etc.), in temporal relation to a trigger event, and/or in any other suitable order at any suitable time and frequency by and/or using one or more instances of the system 200, elements, and/or entities described herein. However, the method 100 and/or system 200 can be configured in any suitable manner.

2. Benefits

In specific examples, the method and/or system can confer several benefits over conventional methodologies for diagnosing patient conditions and prescribing effective treatments. First, given the potential time pressures and complex patient conditions present in conventional healthcare, traditional diagnostic and therapy recommendation approaches can require a significant time investment in order for a care provider to feel confident about the accuracy of a given diagnosis and/or treatment recommendation. Second, a care provider and/or other care provider may not possess the requisite training and/or updated knowledge base (e.g., recent research findings) to sufficiently provide treatment (e.g., medication prescription, titration, etc.) to patients with different user conditions. Third, from a patient perspective, sub-optimal treatment can arise from lack of monitoring (e.g., of effectiveness, of patient response to treatments in natural settings before, during, and/or after treatment provision, etc.) and/or patient adherence to treatment, leading to care providers possessing insufficient response information to make an informed decision on how to modify a current treatment based on a patient's response to the current treatment. As patient data spanning extended periods of time (e.g., obtained through continuous monitoring) can be integral for the iterative process of improving a patient's treatment regimen (e.g., recommending an initial treatment, monitoring responses during a titration period, modifying medication based on the response, etc.), there can be a need for a long-term full-stack solution that interfaces with both patient and provider. Examples of the method 100 and/or system 200 can confer technologically-rooted solutions to at least the challenges described above.

First, the technology can confer improvements in computer-related technology (e.g., digitally provided care provider support; digitally managed treatment response monitoring and analytics; artificial intelligence; computational modeling of diagnosis and treatment determination; etc.) by facilitating computer performance of functions not previously performable. For example, the technology can improve digitally administered care provider support through providing a full-stack solution leveraging passively collected digital communication data, supplementary data, care provider data, and/or other suitable data that would not exist but for advances in mobile devices (e.g., smartphones) and associated digital communication protocols. In a specific example, the technology can provide a full-stack solution starting from monitoring patient digital communication behaviors and patient status before a patient makes an initial visit to a care provider, to providing care providers with relevant patient medical status analysis in real-time during a user-provider interaction, to monitoring patient response to treatments following a user-provider interaction, to providing further decision support for a care provider in deciding whether to modify aspects of the treatment (e.g., type of medication, medication dosage, etc.). Models and/or approaches to generate such analyses and/or recommendations can be iteratively refined to provide such outputs with improved efficiency and specificity for real-time care provider support (e.g., thereby improving the care determination system).

Second, the technology can confer improvements in computer-related technology through an inventive distribution of functionality across a network including a care determination system (e.g., a remote computing system receiving and analyzing digital communication data, supplementary data, interactions with care providers, across a plurality of users), a plurality of mobile devices (e.g., associated with users possessing a diversity of communication behaviors, user-provider relationships, user conditions, and/or other suitable characteristics changing over time), a treatment system (e.g., operable to present medical status analyses including diagnoses and/or therapeutic interventions to care providers, to users, and/or other suitable entities), and/or other suitable components. For example, the care determination system can include functionality of analyzing digital communication data and/or other data previously unused for determining medical status analyses, such as user digital communication data and mobility supplementary data passively collected throughout a treatment regimen (e.g., enabling treatment evaluation based on continuously collected data for pre- and post-treatment provision periods, etc.); digital communication data derived from a population of patients with varying conditions; and/or other suitable data.

Third, the technology can confer improvements in computer-related technology through computer-implemented rules (e.g., feature engineering rules; user preference rules, such as rules describing permissions for types of data collected and/or usable by the care determination system in generating a medical status analysis shared with a care provider; care provider rules, such as rules describing generation of medical status analyses tailored to a care provider to most efficiently guide the care provider; etc.). The increasing prevalence of user digital communication across a plurality of communication protocols and technologies can translate into a plethora of digital communication data (e.g., for both users and care providers), supplementary data (e.g., mobility data, device event data, survey data, etc.), care provider data, and/or other types of data, giving rise to questions of how to process and analyze the vast array of data. However, the technology can address such challenges by, for example, applying feature engineering rules in generating features (e.g., mobility-communication features associated with digital communication behavior and mobility behavior, such as in relation to the treatment regimen) operable to improve processing speed, accuracy, and/or personalization associated medical status analyses and/or other suitable aspects, thereby improving digitally administered care provider support for facilitating improved understanding of patient status.

Fourth, the technology can leverage specialized computing devices (e.g., mobile computing devices with mobility-related sensors, care provider devices, automatic medication dispensers, biosensors, etc.) in facilitating continuous monitoring of a patient (e.g., tracking patient response to recommended treatments), in motivating patient adherence (e.g., by modifying user device operation to alert and/or prompt the user to abide by a treatment regimen based on diagnostic analyses and/or therapy recommendations generated through the method, to automatically control medication dispensation, etc.), and/or providing relevant medical status analysis to the appropriate entities (e.g., at a computing devices of care provider, of a guardian, of a friend, of a family member, etc.). In an example, the technology can apply non-generalized location sensors (e.g., GPS systems) to the novel application of care determination through passive continuous monitoring of a patient throughout a treatment regimen.

Fifth, the technology can improve the technical fields of at least digital communication, computational modeling of user and/or care provider behavior, digital medicine, diagnostic and/or treatment prediction, and/or other relevant fields. For example, the technology can continuously collect and utilize datasets unique to internet-enabled mobile computing devices (e.g., social network usage, text messaging characteristics, application usage, patient response monitoring data facilitated through the mobile computing device, etc.) in order to provide real-time, digitally provided care provider decision support in any user-provider interaction. Such decision support can provide the care provider with confidence in their decisions, as care providers can face patients with complex conditions outside of a care providers comfort zone (e.g., psychological conditions associated with a mental health patient), where the conditions can be worsened by inaptly prescribed medications. Additionally or alternatively, the technology can provide decision support that is based on up-to-date medical research, which can be difficult for a care provider to stay abreast of, thereby aiding a care provider in feeling confident that all potential diagnostic and therapeutic options have been considered. Further, the technology can reduce the time required for a care provider to perform an accurate diagnosis and/or treatment recommendation, which can lead to less care provider stress and better patient care. In another example, the technology can take advantage of such datasets (e.g. patient response data to medication, etc.) to better improve the understanding of mental conditions in the field. In another example, the technology can collect patient digital communication behaviors and/or other suitable behaviors with respect to mobile computing devices, determine correlations between the patient digital communication behaviors and patient medical status (e.g., at high risk of depression, low signs of bipolar disorder, etc.), and present the patient medical status analysis to a care provider in a form tailored to guide the care provider in efficiently and accurately making diagnostic and therapeutic choices for the patient. In a specific example, the technology can provide a care provider with likely diagnoses of a patient, which can aid the care provider in narrowing the number and/or types of diagnostic tests to perform on the patient, thereby leading to faster, cheaper, and more accurate user-provider interactions.

Sixth, the technology can provide technical solutions necessarily rooted in computer technology (e.g., utilizing computer models to extract patient health insights from datasets unique to internet-enabled mobile computing devices, in order to provide real-time decision support to care providers at care provider computing devices; modifying visually perceptible digital elements of medical status analyses to tailor the medical status analyses to improving efficient and accurate digitally administered care provider support; etc.) to overcome issues specifically arising with computer technology (e.g., issues surrounding how to use patient digital communication behavior information to improved diagnostic and therapeutic recommendations for patients; issues surrounding how to improve display of medical status analyses at digital interfaces; etc.).

Seventh, the technology can transform entities (e.g., mobile devices, care determination system, treatment system, users, care providers etc.) into different states or things. In an example, the technology can activate applications executing on user devices and/or care provider devices through providing medical status analyses at the applications. In another example, the technology can provide diagnosis- and therapeutic intervention-support to care providers and/or other suitable digital support, thereby transforming the care provider and the associated care provider devices. In another example, the technology can determine and/or update therapeutic intervention recommendations for improving user conditions, thereby transforming the user condition and the health of the user.

As such, the technology can provide a centralized, full-stack approach to leveraging digital monitoring of, engagement of, and/or treatment of a patient to inform digital administration of care provider support, leading to improved effectiveness and/or efficiency of care delivery, cost savings, and care delivery scalability. The technology can, however, provide any other suitable benefit(s) in the context of using non-generalized computer systems for improving care determination.

3.1 Method—Collecting Communication Behavior Data

Block S110 recites: collecting a log of use dataset associated with user digital communication behavior at a mobile device (e.g., mobile communication device). Block S110 functions to unobtrusively collect and/or retrieve communication-related data (e.g., indicative of digital communication behaviors, mobile application usage, mobile computing device usage, etc.) upon which diagnostic analysis and/or therapeutic recommendations can be inferred. A user is preferably an individual seeking medical attention and/or an individual with a user condition, but can additionally or alternatively be any suitable entity (e.g., human, animal, etc.) possessing any suitable relationship with a care provider. Patient digital behavior data preferably indicates digital behaviors with correlations to medical status (e.g., medical symptom information, diagnostic information, treatment information, treatment efficacy, patient adherence, etc.), but can additionally or alternatively be indicative of any suitable patient characteristic. Collected patient digital behavior data can include logs of use of native communication applications (e.g., phone calling applications, messaging applications, virtual assistant applications, social networking applications, applications facilitating communication with a care provider, etc.), of medical software applications (e.g., cognitive behavioral therapy applications, patient monitoring applications, biosignal detectors, biosensor software, etc.), and/or any suitable data collectable and/or derived from a device of the patient. As such, Block S110 preferably enables collection of one or more of: phone call-related data (e.g., number of sent and/or received calls, call duration, call start and/or end time, location of the user before, during, and/or after a call, and number of and time points of missed or ignored calls); text messaging (e.g., SMS text messaging) data (e.g., number of messages sent and/or received, message length associated with a contact of the user, message entry speed, delay between message completion time point and sending time point, message efficiency, message accuracy, time of sent and/or received messages, location of the user when receiving and/or sending a message, media such as images, charts and graphs, audio, video, file, links, emojis, clipart, etc.); data on textual messages sent through other communication venues (e.g., public and/or private textual messages sent to contacts of the user through an online social networking system, reviews of products, services, or businesses through an online ranking and/or review service, status updates, "likes" of content provided through an online social networking system), vocal and textual content (e.g., text and/or voice data that can be used to derive features indicative of negative or positive sentiments; textual and/or audio inputs collected from a user in response to automated textual and/or voice communications; etc.) and/or any other suitable type of data. However, patient digital behavior data can include any suitable information relevant to efficiently and/or accurately providing diagnostic results and/or treatment recommendations for a patient.

Patient digital behavior data is preferably recorded at a mobile computing device associated with a user (e.g., a smartphone, tablet, smartwatch, laptop, etc., of a user). Additionally or alternatively, patient digital behavior data can be collected from computing devices associated with a care provider (e.g., patient data inputted by a care provider surveying a patient during a doctor appointment), a guardian (e.g., patient data inputted by a guardian administering a medication regimen to a patient), a third party (e.g., database information concerning electronic health records, patient demographic information, patient behavioral information, patient digital communication data, etc.), and/or other suitable entity. In a variation, collecting patient digital behavior data can be performed continuously in real-time as the patient uses a corresponding mobile computing device. For example, as a patient writes and sends a text message, text messaging characteristics (e.g., content, length, recipient, timestamp, time to write, grammar, etc.) regarding the text message can be recorded and transmitted to a remote server for subsequent analysis.

Communications from the log of use are preferably associated with one or more temporal indicators (e.g., during, before, and/or after the user-provider interactions such as visits; time period associated with a treatment regiment, etc.). The temporal indicators can include at least one of: a time period (e.g., seconds, minutes, hours, days, etc.), an absolute time (e.g., indicated by a timestamp), be specific to a user (e.g., a time period associated with a user's daily activity), be specific to a user condition (e.g., a time period associated with medication provision, etc.), be specific to a care provider (e.g., a time period associated with care provider operating hours; etc.), and/or can include any suitable type of temporal indicator. For example, a log of use can include digital communication behavior data collected during a time period (e.g., prior to a user-provider interaction) in which supplementary datasets are collected, where the time period can additionally or alternatively be associated with collected care provider datasets (e.g., care provider data for therapeutic interventions administered to the user to improve symptoms experienced during the time period; user-provider interactions during the time period; care provider inputs commenting upon the log of use data and/or supplementary data collected during the time period; etc.). In an example, generating patient medical status analysis can be based on patient digital behavior data including mobile computing device usage collected over a period of a first and second month, medical device data collected over the second month, a human coach-patient interaction during the second month, and a survey response received in the first day of the first month. Alternatively, generating medical status analysis can be determined from user data associated with the same temporal indicator (e.g., only using data collected during a specific week of the year). Additionally or alternatively, digital behavior data leveraged in determining medical status analysis can have any suitable temporal relationship. However, log of use datasets, other datasets, and associated time periods can be configured and/or related in any suitable manner.

In a variation, collecting patient digital behavior data can be in response to satisfaction of a condition (e.g., a patient engaging in unexpected or high-risk digital communication behavior, a patient permitting a medical monitoring application to record digital behaviors of the patient, a care provider requesting a medical status update for a patient being monitored, treatment response efficacy below an efficacy threshold, a patient requesting a patient medical report to be transmitted to a care provider, and/or any other suitable condition or criteria). However, Block S110 can be performed in any suitable manner.

3.2 Method—Collecting a Supplementary Dataset

Block S120 recites: collecting a supplementary dataset characterizing activity of the user (e.g., in association with a time period), which functions to unobtrusively receive non-communication-related data from a user's mobile device and/or other device configured to receive contextual data from the user. Supplementary datasets can include any one or more of: device sensor datasets (e.g., mobility supplementary datasets; etc.); medical device data; survey datasets; application usage datasets (e.g., social networking datasets; treatment provision application datasets); device usage information (e.g., screen usage information, physical movement of the mobile device, etc.), device authentication information (e.g., information associated with authenticated unlocking of the mobile device); third-party data; and/or any suitable mobile computing device data. Social networking characteristics can include quantitative characteristics (e.g., amount of posts, amount of views, degree of using a social networking feature, number of social networking friends, number of professional contacts, etc.), content characteristics (e.g., post content, comment content, media content, profile content, etc.), change in activity (e.g., change in social network activity, change in posts frequency, change in content tone, change in social network relationships, etc.), and/or any other suitable social networking characteristics. Mobile computing device sensor information can include recorded biosignals (e.g., heart rate, blood pressure, EEG signals, blood sugar levels, etc.), location information (e.g., GPS sensor information), physical activity information (e.g., inertial sensor data including gyroscope data, accelerometer data, etc.), light sensor information (e.g., measuring amount of user light exposure, etc.), and/or any other suitable mobile computing device sensor information. However, mobile computing device usage information can include any other suitable information.

In a variation, Block S120, can include collecting a mobility supplementary dataset. For instance, the supplementary dataset can include a mobility supplementary dataset including a log of times when the user has picked up and/or placed the mobile device down, in able to determine when the mobile device was in use. Such data can be used to flag certain time periods as time periods where the user was awake. In variations, Block S120 can include receiving a mobility supplementary dataset including location information of the user by way of one or more of: receiving a GPS location of the user (e.g., from a GPS sensor within the mobile device of the user), estimating the location of the user through triangulation of local cellular towers in communication with the mobile device, identifying a geo-located local Wi-Fi hotspot during a phone call, and in any other suitable manner. In specific examples, mobility supplementary datasets can include one or more of: user location data (e.g., a user located inside their private house when communicating with a care provider about a treatment regimen, etc.), physical activity data (e.g., footstep parameters; heart rate above a threshold amount exceeding an average resting heart rate while communicating with a care provider and/or care determination system; accelerometer and/or gyroscope data; breathing patterns; other cardiovascular and/or physical activity parameters; physical isolation lethargy; etc.), and/or any other suitable data. For example, Block S120 can include collecting a mobility supplementary dataset indicating the locations of the user within a predetermined time period of the user taking a medication (e.g., before, during, after taking the medication, etc.) for a treatment regimen. In another example, Block S120 can include receiving a mobility supplementary dataset indicating locations at which therapeutic interventions were promoted to the user. However, collecting mobility supplementary datasets can be performed in any suitable manner.

In another variation, Block S120 can include collecting a survey dataset (e.g., survey responses from the patient; patient responses to care provider-administered questions and inputted by a care provider; etc.). A presented survey can prompt for information regarding user demographic, behavior, digital communication activity, current medical status, historical medical status, family medical status and/or any suitable user information relevant to providing diagnostic analyses and therapy recommendations. As shown in FIGS. 17A-17E, in specific examples, a digital survey can be presented to a user, asking for information regarding: demographic information (e.g., gender, ethnicity, age, name), medical history (e.g., previous diagnoses, previous treatments), current medical status (e.g., current medications, current symptoms, current conditions), future plans (e.g., health plans, exercise plans, habits, life plans, etc.), mental condition (e.g., mental thoughts, anxiety, stress, mood, emotions, etc.), and/or other suitable information. However, collecting a survey dataset can be performed in any suitable manner.

In another variation, Block S120 can include collecting usage data for a therapy provision application executing on a mobile computing device of the patient. Therapy provision applications can include any application suitable for and/or designed for facilitating a therapeutic effect on a user (e.g., through administering a therapeutic intervention; etc.). For example, a therapy provision application can include elements related to cognitive behavioral therapy, acceptance and commitment therapy, anger management, mindfulness, couples therapy, trauma relief therapy, and/or any other suitable elements for aiding in psychological ailments (e.g., helping with mood recognition, dealing with negative emotions, overcoming self-esteem issues, striving for positive emotions, handling stress, etc.). However, collecting therapy provision application data and/or other suitable application data can be performed in any suitable manner.

In another variation, Block S120 can include collecting medical device data. Medical device data can be collected from medical devices including any one or more of: a biosensor, a biosignal detector, a mobile computing device executing a medical application, a medication adherence device (e.g., automatic medication dispenser, alert devices, chip-embedded medication), and/or any other suitable medical device. For example, a log of patient usage of an automatic medication dispenser can be used in characterizing patient response to a medication regimen. Additionally or alternatively, the medical device data can be directly used in generating a diagnostic analysis and/or therapy recommendation for the patient. For example, EEG readings can be directly used (e.g., in combination with digital communication behaviors) for diagnosing the risk severity of depression in an at-risk individual. However, collecting medical device data can be performed in any suitable manner.

In another variation Block S120 can include collecting a device event dataset, such as in a manner analogous to that described in U.S. application Ser. No. 13/969,339 filed on 16 Aug. 2013. However, collecting supplementary data can be performed in any suitable manner.

3.3 Method—Collecting Care Provider Data

The method 100 can additionally or alternatively include Block S125, which recites: collecting care provider data (e.g., care professional data), which functions to receive datasets associated with one or more care providers, user conditions (e.g., user-provider interactions relating to the user condition; therapeutic interventions promoted through medical status analyses and/or administered by care providers for the user condition; etc.), and/or other suitable entities. A care provider dataset preferably includes care provider analyses (e.g., regarding components of medical status analyses, regarding the user condition, etc.), survey responses (e.g., responses from care providers to surveys analogous to those described in Block S140), assessments and/or insights regarding user-provider interactions (e.g., communications between one or more users and care providers; in-person communications; textual communications, audio; video; automated communications; communication content; etc.), regarding medical status analyses (e.g., care provider modifications to medical status analyses; care providers' actual diagnosis and/or therapeutic intervention in relation to a medical status analysis' predicted diagnosis and/or therapeutic intervention; care provider inputs associated with medical status analyses, such as comments on diagnoses from medical status analyses; etc.), regarding therapeutic interventions, and/or any other suitable aspects, but can include any suitable data in relation to one or more users. User-provider interactions can be through any one or more of: in-person communication (e.g., a scheduled appointment), digital communication (e.g., text messaging communication), and/or any suitable venue. In another variation, Block S125 can include collecting electronic health records (e.g., from retrieving electronic health records generated from data associated with the method 100; from querying third-party databases; from receiving electronic health records and/or associated data from care providers, etc.), which can be subsequently processed (e.g., through natural language processing; extracting features; etc.) for use in other portions of the method 100 (e.g., determining medical status analyses and/or therapeutic interventions, etc.). However, collecting and/or processing electronic health records can be performed in any suitable manner.

For Block S125, care provider data can be collected through a web interface, an application executing on a mobile device (e.g., a care provider device), and/or any suitable venue. For example, Block S125 can include receiving a care provider dataset in response to prompting a care provider to provide a care provider input (e.g., at a web interface displaying user information including a user improvement evaluation, etc.), such as during and/or after a user-provider interaction (e.g., an in-person visit). In another example, Block S125 can include receiving care provider data in real-time during a user-provider interaction (e.g., where the care provider data includes care-provider interaction data such as the user's answers to the care provider's questions associated with the user condition; etc.). Additionally or alternatively, receiving a care provider dataset can be performed in any manner analogous to embodiments, variations, and examples described in U.S. application Ser. No. 15/005,923, entitled "Method for Providing Therapy to an Individual" and filed on 25 Jan. 2016, which is herein incorporated in its entirety by this reference. However, Block S125 can be performed in any suitable manner.

Blocks S110-S125 preferably include collecting datasets associated with a time period and/or other suitable temporal indicator, where different collected datasets can be: collected during the same time period (e.g., received at the care determination system during the time period; sampled during the time period; etc.); related to datasets collected during the time period (e.g., a care provider dataset including care provider assessments of log of use data collected during the time period; etc.); and/or otherwise associated with temporal indicators. Additionally or alternatively, collecting datasets can include any suitable elements described in U.S. application Ser. No. 15/482,995 filed 10-Apr.-2017, U.S. application Ser. No. 13/969,339 filed 16 Aug. 2013, which are incorporated herein in their entirety by this reference. However, collecting patient digital behavior can be performed in one or more of the approaches described above, and/or performed in any other suitable manner.

3.4 Method—Determining a Medical Status Analysis

Figure 11:
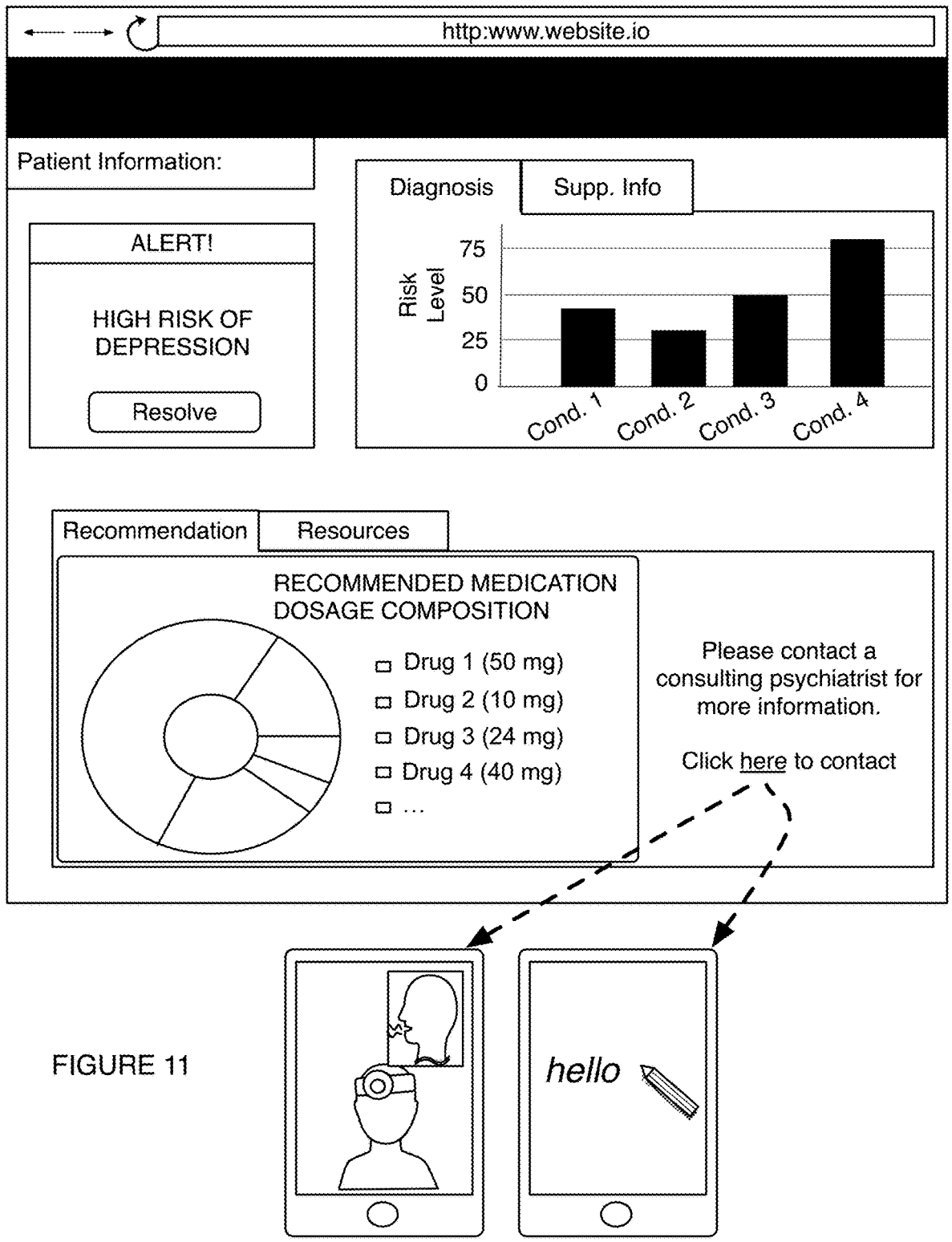
FIGS. 11-13 are schematic representations of examples of presenting medical status analyses.
Figure 12:
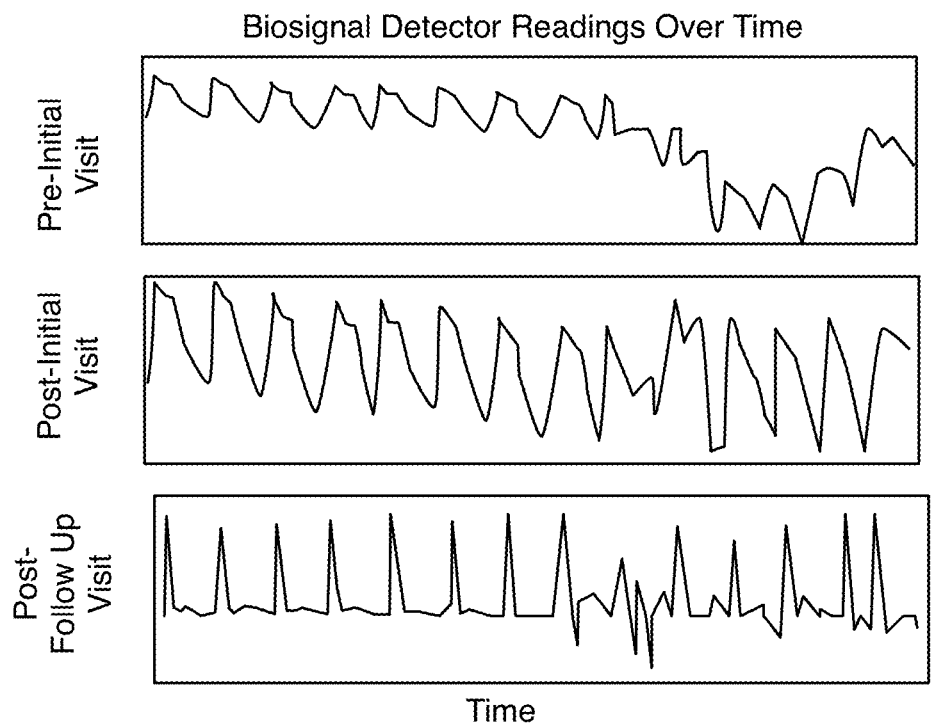
Figure 13:
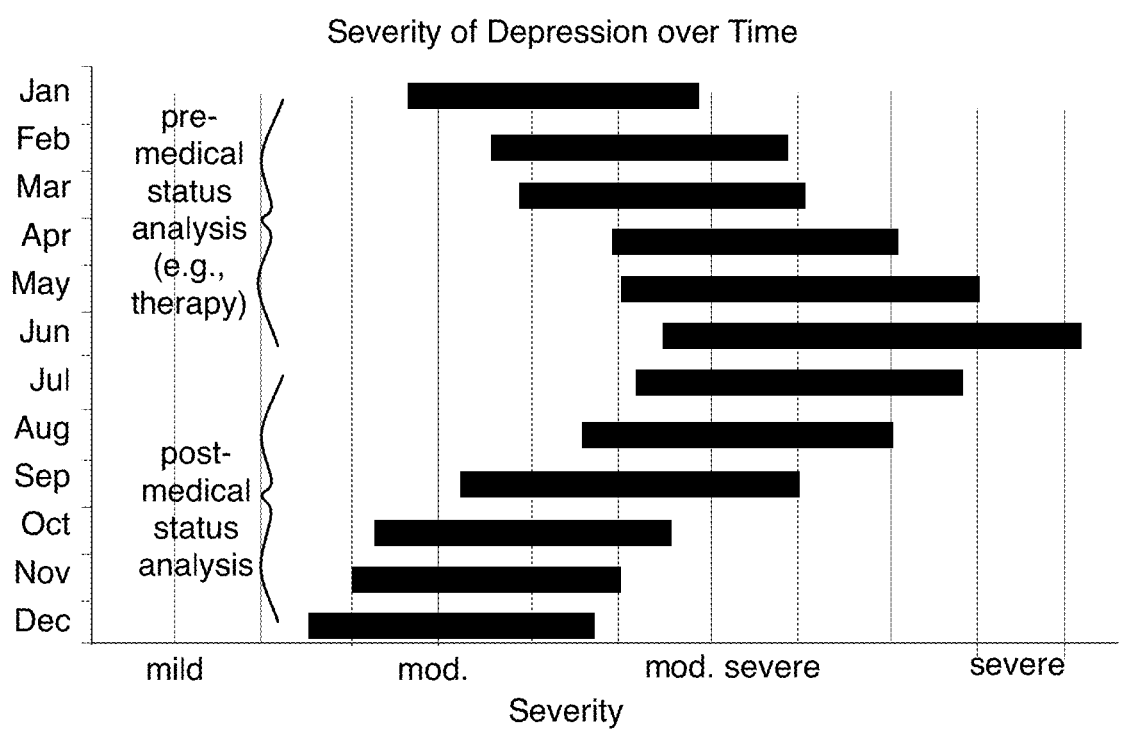

Block S130 recites: determining a medical status analysis (e.g., care status analysis) for a condition of the user based on at least one of a log of use dataset and a mobility supplementary dataset. Block S130 functions determine medically relevant information regarding a user and/or user condition. As shown in FIGS. 11-13, medical status analyses preferably include a diagnosis and/or therapeutic intervention (e.g., a therapy recommendation; treatment recommendation; etc.). Additionally or alternatively, medical status analyses can include symptom information (e.g., predicted current symptoms, potential future symptoms), supplemental user information (e.g., automatically identified demographic information, behavioral information, familial information, etc.), a supplemental medical status analysis (e.g., drug interactions; reasoning components including the sources of information upon which the medical status analysis is based; references to additional information regarding a generated diagnostic analysis and/or therapy recommendation; etc.); user behaviors determined based on datasets collected in Blocks S110-S125; options for care providers to provide care provider data; digital behavior data for other patients; correlations between digital behavior data and conditions; reference patient profiles (e.g., digital behavior profiles of patients with known conditions and/or treatment responses, composite patient profiles, manually curated patient profiles, automatically generated patient profiles, and/or any suitable reference patient profile; etc.); general medical information derived from databases and/or other resources (e.g., Diagnostic and Statistical Manual of Mental Disorders, International Statistical Classification of Disease and Related Health Problems, resources from the American Psychiatric Association, the World Health Organization, drug regulation agencies, health insurance companies, pharmaceutical companies, policy organizations, research organizations, educational institutions, etc.); therapeutic interventions prescribed to patients (e.g., prescribed and/or verified as efficacious for patients sharing the condition, patients with shared medical parameters; etc.); and/or any other suitable information. In a variation, determining a medical status analysis can include automatically ranking (e.g., triaging) users from a set of users (e.g., patients associated with a particular care provider; patients sharing a demographic; patients associated with a hospital; patients sharing a condition; etc.) for assigning degrees of urgency for providing care and/or for determining suitable types of therapeutic interventions for different users. For example, the method 100 can include identifying a subset of users associated with conditions suitable for treatment through a subset of therapeutic interventions (e.g., therapy, psychiatry, specialized care provider visits, etc.). Ranking users can be based on condition, user response monitoring, therapeutic intervention effectiveness, datasets collected in Blocks S110-S125 (e.g., user-provider interaction data, electronic health records, survey data, logs of use, mobility supplementary data, etc.), and/or any other suitable criteria. Additionally or alternatively, such criteria can be used in ranking and/or otherwise evaluating care providers (e.g., determining a metric indicative of the degree to which care providers are following best practices, such as determined based on reasoning components, etc.). For example, evaluating care providers can be based on at least one of user-provider interactions, care provider inputs, electronic health records, and/or other suitable criteria. Ranking users and/or care providers can be performed at any suitable time and/or frequency (e.g., updating the triaging of users based on user response monitoring, such as by updating the ranking associated with a user to recommend therapy for the user, etc.). Rankings can additionally or alternatively be used in determining the timing and/or frequency of determining a medical status analysis and/or in other suitable portions of the method 100 (e.g., determining therapeutic interventions; promoting medical status analyses; etc.), and/or used for any suitable purpose. However, ranking users and/or care providers can be performed in any suitable manner analogous to U.S. application Ser. No. 15/005,923 filed 25 Jan. 2016, which is herein incorporated in its entirety by this reference.

Regarding Block S130, generating medical status analyses is preferably based on datasets collected in Blocks S110-S125. In a variation, Block S130 can be based on log of use data. For example, the method 100 can include identifying correlations between digital communication behavior from a set of users (e.g., population of users) and one or more user conditions (e.g., a correlation between decreased digital communication frequency and severity of depression); determining a medical status analysis for a user based on the correlations and a log of use dataset for the user; promoting a therapeutic intervention according to the medical status analyses; and updating the medical status analysis based on an updated log of use dataset for the user and the correlations (e.g., determining an improvement in depression based on an increase in digital communication frequency for the user in response to the therapeutic intervention; etc.).

In another variation, Block S130 can be based on mobility supplementary datasets. For example, the method 100 can include: identifying a partial response to a promoted medication dosage (e.g., recommended in a medical status analysis) based on log of use dataset and a mobility supplementary dataset (e.g., indicating, during post-therapeutic intervention periods, an increased amount of digital communications at locations of a greater average distance from the user's household, etc.); and updating the medical status analysis (e.g., increasing the medication dosage) based on the identified partial response. However, determining medical status analyses based on mobility supplementary datasets and/or log of use datasets can be performed in any manner analogous to U.S. application Ser. No. 13/969,349 filed 16 Aug. 2013, which is incorporated in its entirety by this reference.

In another variation, Block S130 can be based on interaction data (e.g., collected from log of use data; from care provider data; etc.) for interactions between users and/or care providers. For example, Block S130 can be based on interactions between a user and a plurality of care providers. In a specific example, Block S130 can include: determining (e.g., updating) a medical status analysis based on user-first care provider interaction data between the user and a first care provider (e.g., verbal communications regarding physical symptoms experienced by the user and associated with the user condition, etc.), and user-second care provider interaction data between the user and a second care provider (e.g., textual communications regarding psychological symptoms experienced by the user and associated with the user condition, etc.). In another example, Block S130 can be based on interactions between a care provider and multiple users, such as through personalizing a medical status analysis to a care provider based on interactions between the care provider and their patients (e.g., including therapeutic interventions in a medical status analysis that are commonly recommended by the care provider for a user condition; including summaries of previous interactions between the care provider and patients; including recommended interactions to the care provider based on historic interactions associated with the care provider; leveraging user-provider interactions concerning a first patient in order to provide analogous insights for a second patient of the care provider; etc.). In another example, Block S130 can be based on interactions between care providers. In a specific example, Block S130 can include: determining a medical status analysis based on first care provider-second care provider interaction data for interactions between care providers (e.g., interaction data associated with a first care provider consulting a second care provider concerning the user and/or user condition, such as interaction data concerning symptoms, diagnoses, therapeutic interventions, and/or other suitable components of medical status analyses). Any suitable format of interactions between care providers and/or users can be facilitated at any suitable time. For example, the method 100 can include automatically initiating, during a user-care provider interaction period (e.g., during an initial visit; follow-up visit; digital communication period; etc.), a telemedicine communication through a wireless communicable link between a first care provider device associated with the first care provider, and a second care provider device associated with the second care provider; and collecting the first care provider-second care provider interaction data based on the telemedicine communication (e.g., transcribing the telemedicine communication; analyzing the transcription; etc.).

In another variation, Block S130 can be based on one or more user conditions. For example, Block S130 can include determining reasoning components (e.g., information sources associated with the user condition) of a medical status analysis based on the condition (e.g., mapping the user condition to a plurality of information sources associated with diagnosis and/or therapeutic interventions for the user condition; determining the medical status analysis based on the information sources; etc.). In another example, Block S130 can include modifying a visually perceptible digital element of the medical status analysis based on a user condition (e.g., using colors, fonts, graphics, and/or other suitable format components for highlighting portions of the medical status analysis to optimize care determination by a care provider, such as highlighting user conditions with high risk; highlighting side effects of a promoted therapeutic interventions; etc.), where the visually perceptible digital element can be associated with the reasoning component (e.g., highlighting the primary information sources from which the diagnosis is based, etc.) and be operable to improve display of the care status analysis. Additionally or alternatively, modifying perceptible elements of medical status analyses can be based on any suitable criteria. However, determining medical status analyses based on any suitable data can be performed in any suitable manner.

Regarding Block S130, determining a medical status analysis is preferably based on one or more medical status features. Medical status features can include any one or more of: mobility features (e.g., location, physical activity behaviors, inertial sensor data, etc.), user condition features (e.g., diagnostic features; user response to therapeutic interventions; survey response data; etc.), textual features (e.g., word frequency, sentiment, punctuation associated with words present in text messages; length; textual features extracted from transcriptions of phone calls associated with the user; etc.), graphical features (e.g., emojis used in text messages; media posted to social networking sites; media transmitted and/or received through digital messages; associated pixel values; etc.), audio features (e.g., Mel Frequency Cepstral Coefficients extracted from audio captured in telemedicine communications, phone calls; etc.), cross-user features (e.g., average frequency of text messages; average length and/or duration of phone calls and/or text messaging; users participating in a digital communication; etc.), cross-care provider features (e.g., care provider communication features associated with subgroups of care providers, etc.), and/or any other suitable features.

Regarding Block S130, determining medical status features is preferably based on applying one or more computer-implemented rules (e.g., a feature engineering rule; a user preference rule; rules operable to improve care determination systems, treatment systems, and/or associated medical status models, etc.), but medical status features can be determined based on any suitable information. In an example, Block S130 can include establishing and/or storing computer-implemented rules (e.g., to be used in determining the medical status analysis) based on one or more reasoning components (e.g., third-party information sources; meta-analysis performed on data associated with different portions of the method 100, such as user response monitoring data). In another example, Block S130 can include obtaining a first feature engineering rule defining a medical status analysis as a function of at least one of log of use data and mobility supplementary data; and generating mobility-communication features (e.g., digital communication frequency and/or duration at particular locations; physical activity behaviors in relation to digital communication behaviors; etc.) and/or other medical status features based on evaluating the at least one of the log of use data and the mobility supplementary data against the first feature engineering rule. In another example, Block S130 can include obtaining a second feature engineering rule operable to associate the mobility-communication features (and/or other medical status features) with care provider data; and modifying the features based on the care provider data (e.g., labeling the features with care provider inputs concerning the patient behaviors indicated by the features; presenting patient behaviors in a medical status analysis to a care provider, and enabling the care provider to collect and transmit patient responses concerning the patient behaviors, which can be used to generate and/or label medical status features). In a specific example, mobility-communication features including digital communication frequency outside the user's household can be associated with user-provider interaction data indicating a user's severity of anxiety associated with the digital communication frequency. However, applying medical status features can be performed in any suitable manner.

Figure 4:
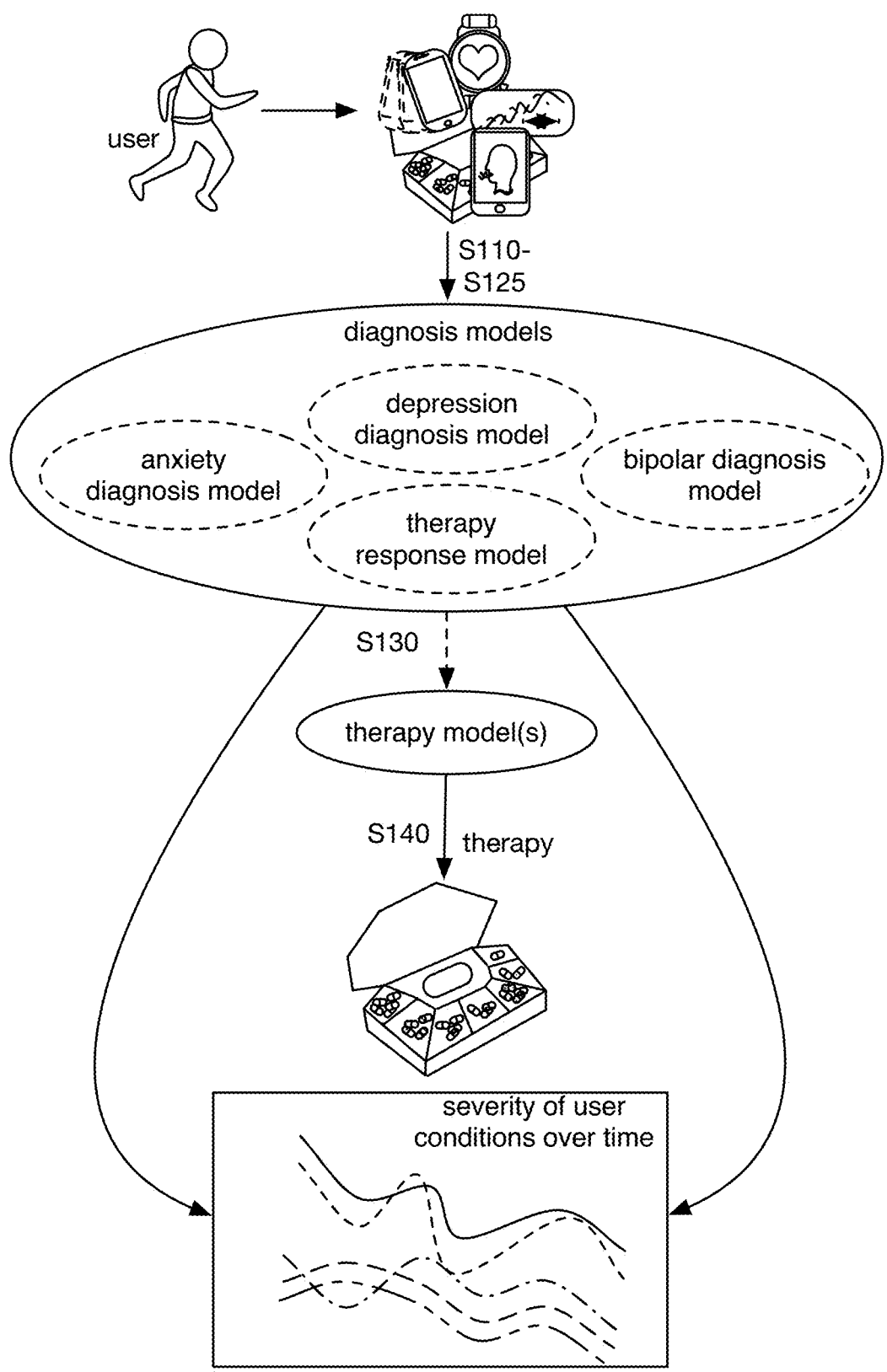
FIG. 4 is a schematic representation of a variation of a method for improving care determination using multiple models.

Block S130 can additionally or alternatively include generating, applying, and/or otherwise manipulating medical status models, which preferably output one or more components of a medical status analysis based on data collected in Blocks S110-S125 and/or other suitable inputs. As shown in FIG. 4, medical status models can include diagnosis models (e.g., depression diagnosis model; anxiety diagnosis model; bipolar diagnosis model; therapy response models; etc.), therapy models, and/or any other suitable models. In an example, Block S130 can include determining a diagnosis with a diagnosis model; and determining a therapeutic intervention with a therapeutic intervention model based on the diagnosis. In another example, Block S130 can include, in response to collecting a care provider dataset (e.g., including user-provider interaction data) during a user-care provider interaction period: retrieving the diagnosis model and/or therapeutic intervention model during the user-care provider interaction period; and updating the medical status analysis in real-time during the user-care provider interaction period based on the diagnosis model, the therapeutic intervention model, and the care provider dataset.

In a variation of Block S130, generating patient medical status analysis includes generating a decision tree model with internal nodes and branches selected based on correlations between digital behavior data and medical statuses (e.g., correlations between different phone calling characteristics and depression), and identifying a medical status of a patient (e.g., a diagnosis, a treatment recommendation, etc.) based on the decision tree. In another variation, generating patient medical status analysis includes employing a machine learning model. Machine learning algorithms for medical status models and/or other suitable models can include algorithms analogous to those described in U.S. application Ser. No. 15/265,454 filed on 14 Sep. 2016. In specific examples, Block S130 can include training and applying a reinforcement learning model (e.g., deep reinforcement learning model), such as a reinforcement learning model for maximizing a reward (e.g., optimizing therapeutic interventions for improving user response in relation to use conditions; personalizing medical status analyses for optimizing care provider support, such as in relation to time spent by the care provider during patient visits; optimizing for care provider confidence in diagnoses and/or recommended therapeutic interventions; etc.), and/or any other suitable type of reinforcement learning models.

Block S130 can additionally or alternatively include updating medical status models. In an example, the method 100 can include presenting a diagnosis and a therapeutic intervention to a care provider based on one or more medical status models; receiving care provider validation (e.g., included in care provider data) of the diagnosis and/or therapeutic interventions at an application executing on a care provider computing device; generating a second model based on the care provider validation; monitoring user response to the therapeutic intervention over the course of a time period; generating an updated medical status analysis using the second model based on the monitored patient response data; and providing decision support to the care provider at a follow-up visit based on the updated medical status analysis. In another example, the method 100 can include: determining an expected patient response based on a care provider-validated diagnosis and/or therapeutic intervention; and generating an updated diagnosis and/or therapeutic intervention based on a comparison between the expected patient response and the monitored patient response data. However, medical status models can be otherwise used and/or updated.

Regarding Block S130, types of medical status analyses can vary across different stages of the patient care process. For example, a diagnosis model and a first therapy model can be operable to generate diagnostic results and an initial medication recommendation for a patient during an initial visit to a care provider, and a second therapy model tailored for modifying the initial medication recommendation can be used in a follow-up visit based on treatment response monitoring data collected between the initial visit and the follow-up visit. However, generating medical status analysis in relation to different periods in the user-provider relationship timeline can be performed in any suitable manner.

In relation to Block S130, generating medical status analyses is preferably in response to receiving a user request for patient medical status analysis to be transmitted to an entity (e.g., a care provider). Generating medical status analysis can be performed in real-time, such that medical status analysis can be generated during a patient's visit with a care provider. In a specific example where the user has provided permission for medical status analysis to be shared with a care provider, a care provider can request (e.g., at an application executing on a care provider mobile computing device) the medical status analysis for the user during the user-provider, and in response to the care provider request, patient medical status analysis can be automatically generated for transmission to the care provider (e.g., to the care provider mobile computing device).

Additionally or alternatively, generating medical status analysis can be performed according to a generation schedule (e.g., generation frequency) for the medical status analysis (e.g., generating the medical status analysis according to when the medical status analysis is to be transmitted to the target destination), which can be based on at least one of: a user and/or care provider schedule (e.g., accommodating for when a patient will be having an appointment with the care provider, for when the care provider has an opening in their schedule to receive and assess the patient's medical status analysis), time intervals (e.g., generation at every minute, hour, day, week, etc.), preferences (e.g., patient preferences, care provider preferences, etc.), data characteristics (e.g., based on a sufficient amount and/or type of collected data to be able to generate patient medical status analysis with a high degree of confidence), stage in the patient care process (e.g., generating medical status analyses with greater frequency post-therapeutic intervention provision; etc.), diagnosis and/or condition (e.g., generating medical status analyses with greater frequency for conditions of greater severity, etc.), and/or any other suitable criteria. For example, Block S130 can include determining a medical status generation schedule (e.g., generation frequency) based on the diagnosis associated with the condition, where updating the medical status analysis includes updating the medical status analysis based on the medical status generation schedule (e.g., generating a medical status analysis every day after a user's daily consumption of medication, etc.) and/or other suitable datasets (e.g., care provider datasets). However, generating medical status analysis can be performed at any suitable time and frequency.

Figure 3:
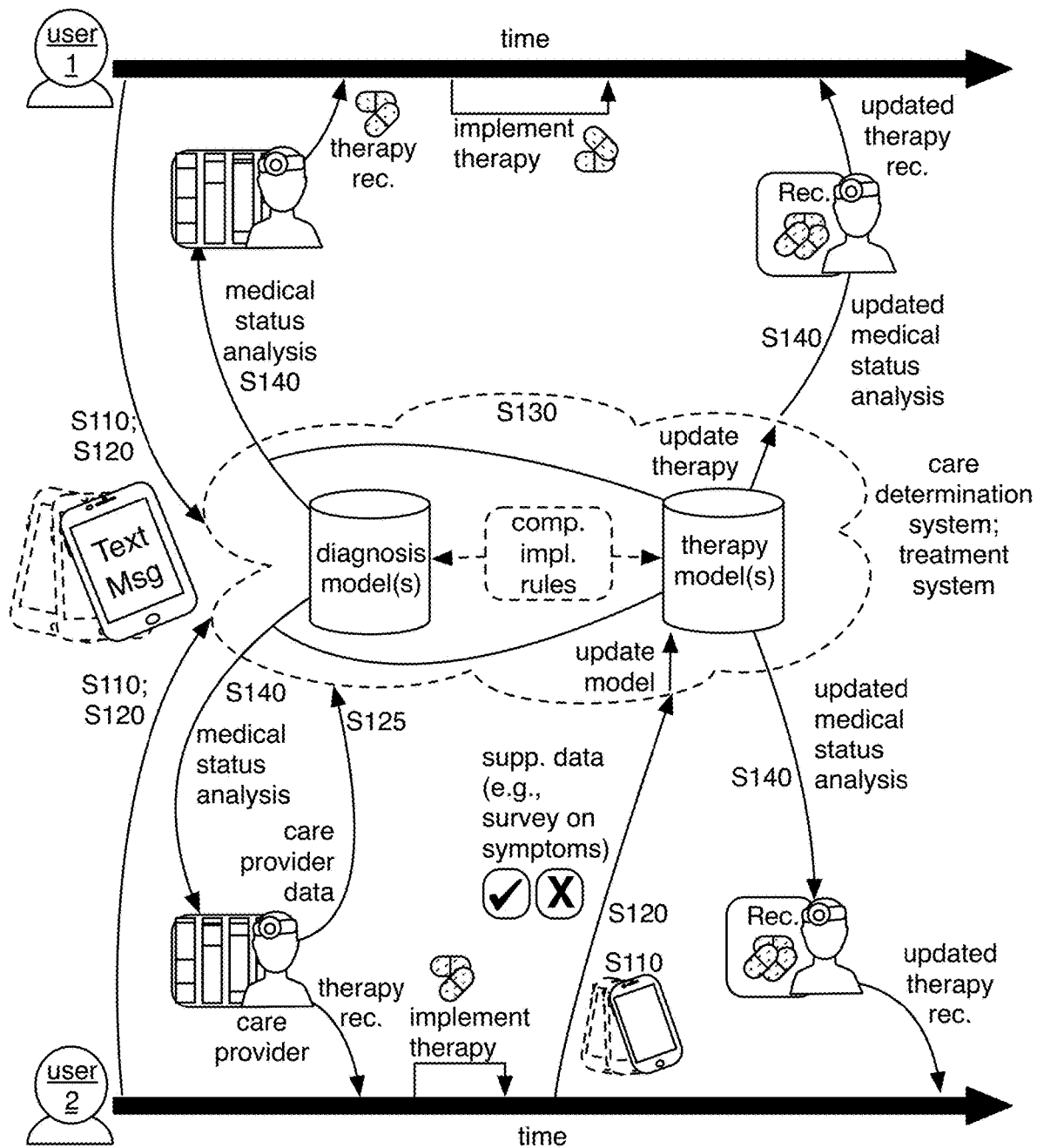
FIG. 3 is a schematic representation of a variation of a method for improving care determination associated with multiple users.

As shown in FIG. 3, generating medical status analysis can be performed for a single patient, concurrently for multiple patients (e.g., by leveraging parallel computing principles and thereby improving the efficiency of the computing system), concurrently for different types of user condition, types of medical status analyses (e.g., concurrently running a diagnosis model and a therapy model), concurrently for multiple care providers, and/or with any suitable sequence for any suitable combination of entities. However, generating medical status analysis can be performed at any suitable time and frequency.

Block S130 can additionally or alternatively include matching a user to a care provider, which functions to identify a care provider suited to provide personalized care to the user. For example, the method 100 can include: determining effectiveness of the therapeutic intervention; in response to the effectiveness satisfying a threshold condition (e.g., a user response below a threshold), determining a match between a user and a first care provider (e.g., a specialist for the user condition, etc.) based on at least one of a log of use dataset, a mobility supplementary dataset, a diagnosis, and/or other suitable data; and presenting the match to a second care provider (e.g., a recommendation for a consulting entity). A consulting entity (e.g., a care provider) is preferably patient-approved (e.g., consultants that the patient has previously seen, that the patient has previously pre-approved such as through an medical monitoring application executing on a patient mobile computing device, etc.). Automatic selection of potential consultants can be based on care provider characteristics (e.g., care provider experience with the platform, care provider experience with given conditions, care provider relationship with the patient, care provider relationship with other care providers, care provider expertise, etc.), patient characteristics (e.g., patient situation, diagnosis, response, digital behavior data, etc.), consultant characteristics (e.g., consultant profession, consultant expertise, consultant experience, etc.), communication considerations (e.g., wireless connectivity, form of communication preferences, language barriers, demographic information, etc.), and/or any other suitable criteria. In a specific example, the method can include: collecting patient digital communication behavior in relation to patient text messaging characteristics associated with a mobile computing device, generating a social anxiety score for the user based on the patient text messaging characteristics, ranking a set of care provider profiles based on professional experience in relation to social anxiety and socially anxious patients, and presenting care provider profiles to the user for initiating a user-provider relationship and transmission of a patient medical status analysis based on the social anxiety score and the ranking of the set of care provider profiles. Additionally or alternatively, matching users to care providers can be performed in any suitable manner. However, Block S130 can be performed in a manner analogous to that described in U.S. application Ser. No. 15/482,995 filed 10 Apr. 2017, which is incorporated in its entirety by this reference, and/or in any suitable manner.

3.4.A Generating a Diagnostic Analysis

As shown in FIGS. 1C, 2-3, and 14A-14C, Block S130 preferably includes determining one or more diagnoses, which functions to determine information regarding one or more user conditions for a user. A diagnosis can include one or more of: a risk and/or severity value indicating a probability of a patient being afflicted with a given condition, general mental or physiological health indicators, comparisons with other groups of individuals (e.g., based on demographic and/or behavioral characteristics shared between the patient and the group of individuals), prevalence information (e.g., prevalence of depression in a given population), symptom information, and/or any other suitable diagnostic information.

In a variation, a diagnosis can be generated without care provider data. For example, a diagnostic analysis can be generated based on collected patient digital behavior data, where the diagnostic analysis is provided to the care provider without the care provider needing to input any patient information. In another variation, generating a diagnostic analysis can be based on collected user data (e.g., log of use data, mobility supplementary data, etc.) and care provider data. In a specific example, a preliminary diagnostic analysis can be generated without care provider input and presented to the care provider during an initial visit between a care provider and a patient. The preliminary diagnostic analysis can guide further diagnostic steps that can be taken by the care provider (e.g., a series of questions to ask the patient). The care provider can input patient data (e.g., patient answers to care provider questions) into a computing device (e.g., an application executing on the smartphone of the care provider), where generating medical status analysis can include generating an updated diagnostic analysis based on the care provider-inputted data. Additionally or alternatively, generating a diagnostic analysis can include any suitable elements described in application Ser. No. 15/069,163 filed 14 Mar. 2016, which is incorporated herein in its entirety by this reference, and/or can be performed in any suitable manner.

3.4.B Determining a Therapeutic Intervention

Block S130 preferably includes determining one or more therapeutic interventions, which functions to analyze user behaviors and/or diagnoses to identify therapeutic interventions for improving a user condition. Therapeutic interventions can include any one or more of: patient medical reports, therapeutic intervention recommendations (e.g., instruction for a guardian, health professional, care provider, and/or any other suitable individual to follow in implementing the therapy recommendation, which can facilitate therapy implementation, for example, in situations where a patient is incapable of fully implementing the therapy recommendation; etc.); health-related notifications (e.g., health tips provided through automated communications, etc.); therapy interventions (e.g., cognitive behavioral therapy exercises; etc.); care provider-related interventions (e.g., telemedicine; scheduling care provider appointments; etc.); physical interventions (e.g., breathing exercises; meditation exercises; acupuncture; hypnosis; brain stimulation such as through magnetic pulses and/or electrical stimulation; etc.); dietary interventions (e.g., probiotics, nutritional supplements, etc.); medication interventions; auditory interventions (e.g., controlling the mobile device to emit music samples in accordance with music therapy; controlling a personal assistance device to vocally emit content components of automated communications, such as with a tone determined based on a format component; etc.); mobile device and/or supplementary medical device interventions (e.g., modifying device operation parameters; etc.); ambient environment interventions (e.g., modification of light parameters, air quality and/or composition parameters, temperature parameters, humidity parameters; etc.) and/or any other suitable types of interventions. Medication interventions can include one or more of: medication type (prescription, over-the-counter, small-molecule, biopharmaceutical, recombinant proteins, vaccines, antibodies, gene therapy, cell therapy, blood products, etc.), medication origin (e.g., herbal, plant, microbial, animal, chemical synthesis, genetic engineering, radioactive material, etc.), dosage (e.g., frequency, amount, time, dosage form, etc.), instructions (e.g., how to implement the medication regimen, after a meal, on an empty stomach, etc.), medication interactions (e.g., with another drug, etc.), results information (e.g., research supporting the type of medication, publications citing the recommended dosage, etc.), supplemental resources (e.g., hyperlinks to additional information about the medication regiment, etc.), and/or any other suitable medication parameters.

Figure 2:
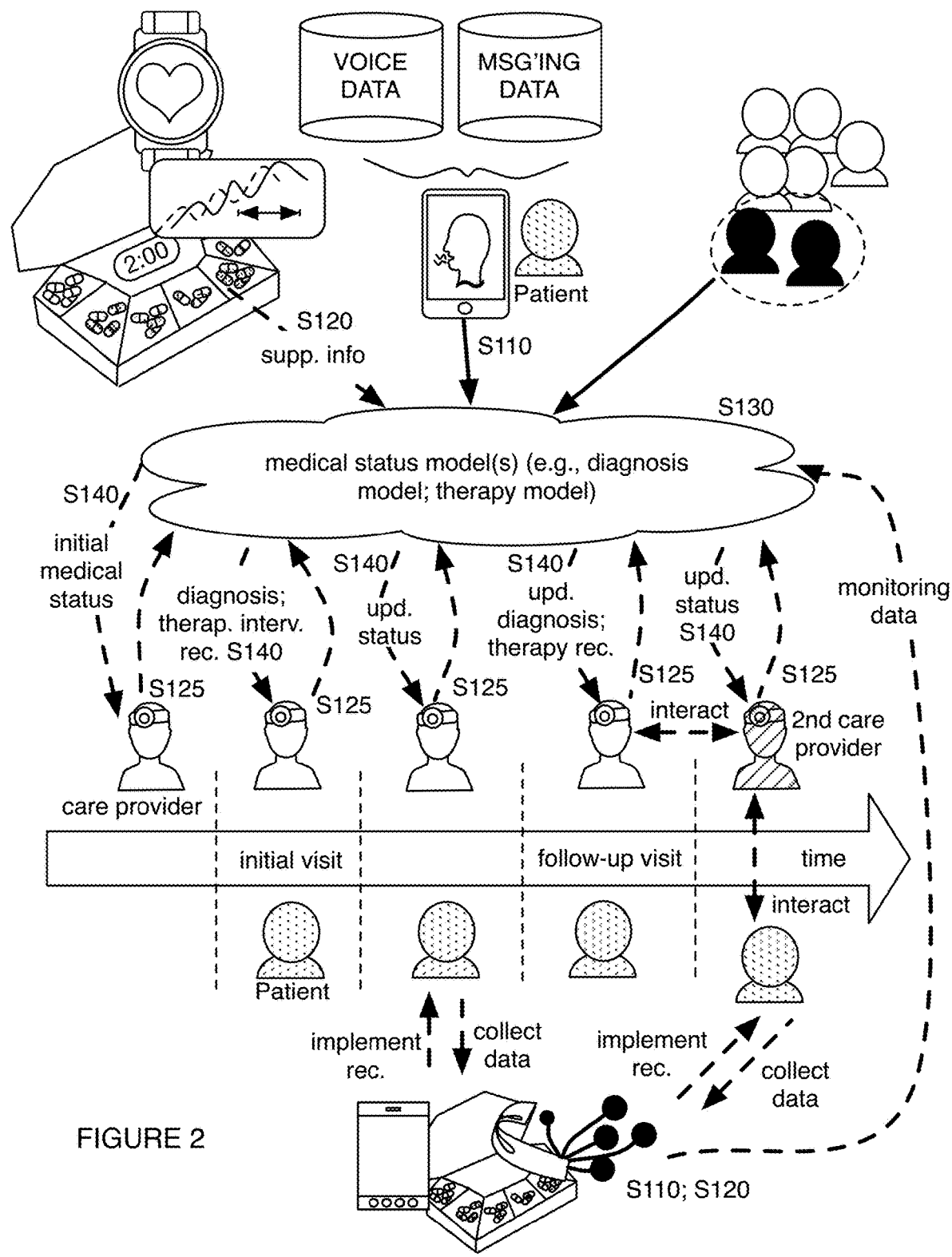
FIG. 2 is a schematic representation of a variation of a method for improving care determination.
Figure 10:
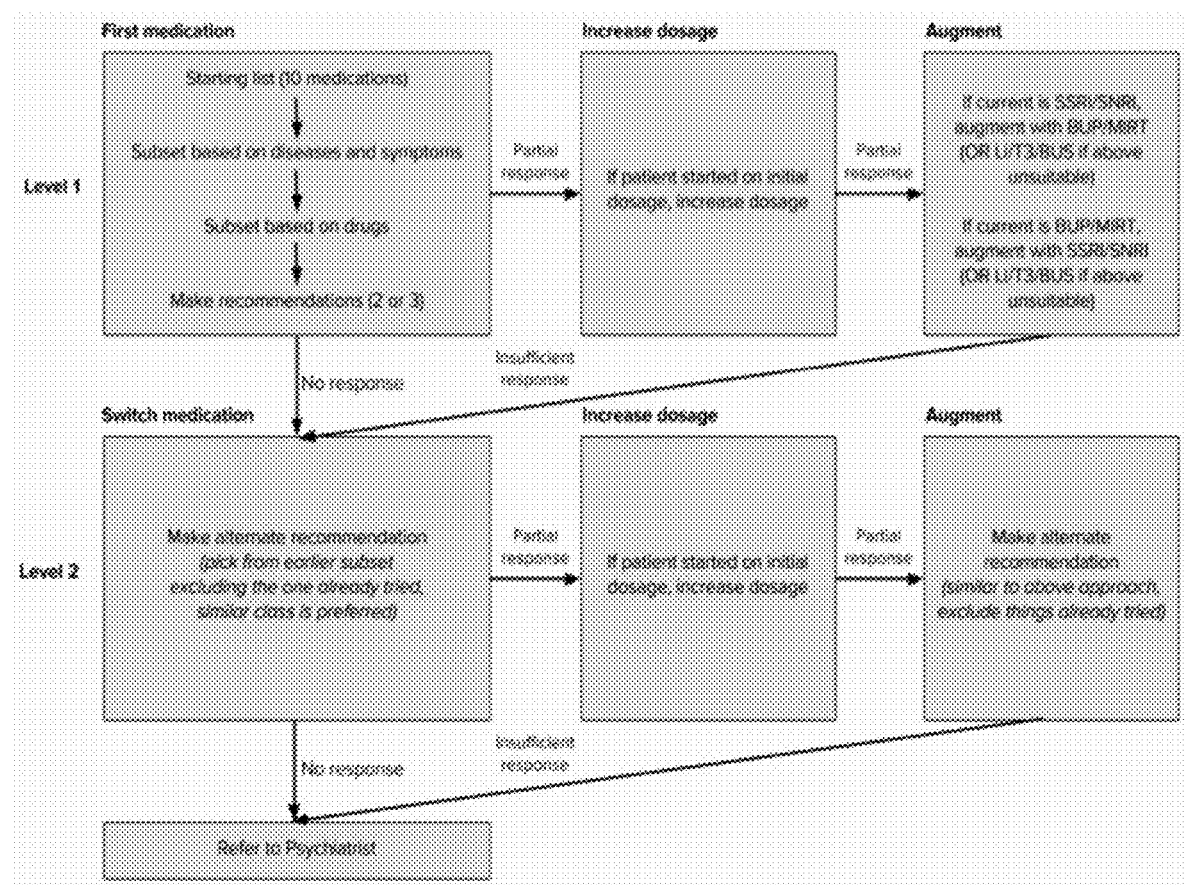
FIG. 10 is a schematic representation of a decision flow for promoting therapeutic interventions according to a variation of a method.

As shown in FIGS. 2 and 10, in a variation, determining therapeutic interventions can be performed for multiple stages of a user-provider relationship. In a specific example, Block S130 can include selecting an initial list of potential therapeutic interventions, narrowing the initial list based on patient digital behavior information, symptoms, drug information, and/or other suitable information, and presenting the narrowed list of potential therapies to a care provider for providing decision support. Additionally or alternatively, a prioritized list of therapeutic interventions (e.g., prioritized based on strength of model recommendation) can be presented to the care provider. User response to the therapeutic interventions can be monitored (e.g., through data collected in Blocks S110-S125, etc.) and used in updating therapeutic interventions, which can include one or more of: modifying dosage (e.g., increasing or decreasing dosage, changing frequency, etc.), augmenting the medication regimen (e.g., adding medication types, removing medication types, etc.), switching a medication type, and/or any other suitable modifications. For example, if a patient exhibits no response to medication "A", then a therapy recommendation modification of switching to medication "B' can be generated and presented to the care provider. If a patient exhibits a partial response to medication "A", then dosage parameters for medication "A" can be altered (e.g., increased dosage). Additionally or alternatively, updating therapeutic interventions can be performed for any suitable number of stages of a user-provider relationship (e.g., multiple stages of partial or no response to medications, and corresponding updates to therapeutic interventions in response to the partial or no response, etc.). However, determining therapeutic interventions can be performed in any suitable manner.

3.5 Method—Promoting a Medical Status Analysis

Block S140 recites: promoting one or more medical status analyses (e.g., diagnoses, therapeutic interventions), which functions to present, provide, administer, and/or otherwise promote one ore more components of a medical status analyses to users, care providers, and/or other suitable entities for improving care determination by a care provider. Promoting medical status analyses can include one or more of: transmitting and/or presenting medical status analyses; guiding care provider decision-making based on medical status analyses (e.g., interactive step-wise decision making tool, etc.); facilitating digital communication (e.g., between a first and a second care provider, such as between a health coach and a licensed therapist; between one or more patients and one or more care providers, etc.); promoting provision of therapeutic interventions from the medical status analyses (e.g., automatically generating medication prescriptions, transmitting prescriptions to pharmacies, automatically scheduling a future care provider appointment, facilitating healthcare payment, aiding with healthcare insurance logistics, controlling user devices to administer the therapeutic intervention; etc.), and/or other suitable processes.

Regarding Block S140, promoting medical status analyses can be performed at specified time intervals (e.g., providing a set of digital patient medical reports to a care provider at the beginning of each day), according to a care provider appointment schedule, for any stage of a user-provider relationship, based on preferences (e.g., a user preference, a care provider preference, etc.), based on rules (e.g., providing decision support in response to disease severity levels exceeding a established threshold, etc.), and/ or at any suitable time. Block S140 is preferably performable in real-time (e.g., during a user-provider interaction, immediately upon request for decision support, etc.), in order facilitate the provision of time-sensitive information (e.g., patient medical information relevant to accurately diagnosing patient issues and providing therapeutically effective treatments, etc.) during a limited time window of the user-provider interaction. However, Block S140 can be performed at any suitable time and frequency.

In a variation, promoting medical status analyses can be performed at multiple instances for a user (e.g., over the course of a user-provider relationship, at different stages of the patient care process, etc.). For example, Block S140 can include promoting a medical status analysis for an initial user-provider interaction (e.g., initial visit), monitoring effectiveness of a therapeutic intervention based on patient response to the therapeutic intervention, and promoting an updated medical status analysis at a follow-up user-provider interaction based on the effectiveness. In a specific example, promoting medical status analyses can include providing a first medical status analysis (e.g., a preliminary patient medical report detailing a preliminary diagnosis without an associated therapeutic intervention) to a care provider prior to an initial interaction between the care provider and patient; providing a second decision support (e.g., an updated patient medical report detailing a comprehensive diagnosis with corresponding therapeutic interventions) in real-time to a care provider during the initial interaction and in response to receiving user-care provider interaction data including user responses to care provider questions administered at the initial interaction; collecting patient response supplementary data concerning a care provider-recommended therapeutic intervention; providing a third medical status analysis (e.g., notifications alerting the care provider to how the patient is responding to the care provider-recommended therapeutic intervention) based on the collected patient response supplementary data and prior to a follow-up interaction between the care provider and the patient; providing a fourth medical status analysis (e.g., facilitating a digital communication between a care provider and a consultant to aid a care provider in utilizing a follow-up digital patient medical report analyzing the patient's response to the care provider-recommended therapeutic intervention and providing suggestions to modify the treatment regimen, etc.) to the care provider during the follow-up interaction, and providing a fifth medical status analysis (e.g., a digital update informing the care provider of the efficacy of the modified treatment regimen; facilitating a digital communication between the care provider and the patient to check on the patient's status) to the care provider after the follow-up interaction. However, performing Block S140 in multiple instances can be performed in any suitable manner.

In another variation, Block S140 can include automatically promoting medical status analyses based on satisfaction of a threshold condition (e.g., a risk of depression exceeding a risk threshold). Threshold conditions can be based on diagnoses (e.g., risk thresholds, severity thresholds, type of user condition thresholds, etc.), therapeutic interventions (e.g., type of therapeutic intervention, urgency associated with a patient needing to start a medication regimen, etc.), data collected in Blocks S110-S125, and/or any other suitable information. However, performing Block S140 based on satisfaction of a threshold condition can be performed in any suitable manner. In another variation, Block S140 support can include promoting a medical status analysis based on a care provider schedule. For example, the method 100 can include receiving a care provider schedule (e.g., at a care determination system), analyzing the care provider schedule for appointment information with a set of patients, and promoting medical status analyses based on the appointment information. In a specific example, receiving a care provider schedule can be in response to presenting an option (e.g., at an application executing on a care provider computing device) for a care provider and/or related individual to sync a care provider schedule of patient support, and Block S140 can include providing the care provider with a digital patient medical report of a set of digital patient medical reports in accordance with the upcoming patient appointments, with patients for an entire day, week, and/or in accordance with any suitable characteristic of the care provider schedule. In another specific example, Block S140 can include receiving a care provider schedule, identifying a patient appointment scheduled for a subsequent day, medical status analyses can be transmitted prior to user-provider interactions, where the medical status analyses can be accessible by the care provider at a care provider device during offline operation (e.g., during the user-provider interaction) and/or when the care provider device is online-enabled. However, performing Block S140 according to a care provider schedule can be performed in any suitable manner.

Block S140 can additionally or alternatively be based on care provider characteristics (e.g., expertise of care provider, demographic information, behavioral information, background of care provider, preferences, etc.), patient characteristics (e.g., patient preferences, patient communication behaviors, demographic information, behavioral information, etc.), and/or any other suitable data. In a variation, Block S140 can include tailoring promotion of a medical status analysis to a care provider based on care provider characteristics. For example, medical status analyses can be modified to suit the designated learning style of the care provider (e.g., providing graphical digital patient medical reports for a visual care provider learner, providing audio digital patient medical reports for an audio care provider learner, etc.). In another example, medical status analysis can be adjusted for the expertise of the care provider (e.g., providing more fundamental mental disorder knowledge for a care provider who is less-experienced in mental conditions but is treating a user with a psychiatric condition, etc.). In another variation, Block S140 can include tailoring promotion of a medical status analysis based on patient characteristics including one or more: genomic characteristics, microbiome characteristics, behavioral characteristics, demographic characteristics, individual characteristics, population characteristics, and/or any other suitable information. For example, Block S140 can include recommending specific communication approaches to the care provider for accommodating the communication behavior (e.g., derived from datasets from Blocks S110-S125) of the patient, received by a mental health patient. However, promoting medical status analyses based on care provider characteristics and/or user characteristics can be performed in any suitable manner.

Block S140 can additionally or alternatively include providing a patient medical report (e.g., a comprehensive report detailing a diagnosis, a therapeutic intervention recommendation, etc.) to a care provider, based on one or more medical status analyses. As shown in FIGS. 14A-14C, 15A-15C, and 16, a patient medical report can include one or more of a diagnosis (e.g., severity of medical issue, risk values, type of condition, etc.), a therapeutic intervention recommendation (e.g., medication types, dosages, drug interactions, supplemental information), user demographic information (e.g., name, sex, age), treatment response information (e.g., digital behavior data collected in response to patient implementation of a medication regimen, biosignal data, survey response data, etc.), reasoning components (e.g., sources of data used in determining components of the medical status analysis, etc.), user history with care providers (e.g., length of working with a health coach, a health professional, etc.), user medical history (e.g., reported symptoms, diagnoses, treatments, family history, etc.), recommendations for other care providers (e.g., contact information of a health professional who can help with treatment, etc.), and/or any other suitable information. In a variation of Block S140, a patient medical report can include digital references. Digital references are preferably capable of activation when a care provider computing device is in online operation (e.g., when a care provider computing device transitions from offline operation to online operation), but can alternatively be capable of activation by a care provider whether the care provider computing device is in an offline or online mode. Digital references can include hyperlinks, digital requests (e.g., to a remote server to perform a particular operation), and/or any suitable content. Hyperlinks can link to supplemental resources (e.g., in-depth medication information such as detailed descriptions, exhaustive list of drug interactions, detailed explanatory analysis of how medication recommendations were determined), updated versions of a medical status analysis (e.g., an updated patient medical report based on up-to-date patient data collected from patient smartphone usage), and/or any suitable additional information. In a specific example, a patient medical report can be provided to a care provider for a patient a week before a scheduled user-provider interaction, the patient medical report including digital references to digital destinations (e.g., a website, an application executing on the care provider device, a remote server, etc.) that, when activated, can transmit a request to a care determination system to execute a care status model on up-to-date data for the patient, thereby updating a patient medical report. Additionally or alternatively, providing a patient medical report can be performed in any suitable manner. However, Block S140 can be performed in any suitable manner analogous to U.S. application Ser. No. 15/482,995 filed 10 Apr. 2017, which is incorporated in its entirety by this reference, and/or in any suitable manner.

3.6 Method—Determining a Subgroup

The method 100 can additionally or alternatively include Block S150, which recites: determining one or more subgroups (e.g., user subgroup, care prouder subgroup), such as with the care determination system and/or other suitable components. Block S150 functions to group one or more users and/or care providers based on shared behaviors (e.g., derived from datasets from Blocks S110-S125, etc.) in order to facilitate determination of medical status analyses. For example, Block S150 can include: assigning the user to a user subgroup of a set of user subgroups, based on digital communication behaviors and/or mobility supplementary behaviors (e.g., grouping users who infrequently digitally communicate and have a mobility within a predetermined distance threshold from their household), and/or care provider data (e.g., grouping users based user condition information provided by care providers; grouping users based on their behaviors towards user-provider relationships, such as determined from user-provider interactions; etc.), where the user subgroup can share a behavior (e.g., mobility-communication behavior) and can be operable to improve care determination for the condition (e.g., through generation and application of medical status models tailored to the subgroup, etc.); and determining the medical status analysis based on the user subgroup and/or other suitable data (e.g., mobility-communication features, care professional data, etc.). However, determining and/or leveraging subgroups can be performed in any suitable manner analogous to U.S. application Ser. No. 15/482,995 filed 10 Apr. 2017, and/or U.S. application Ser. No. 13/969,339 filed on 16 Aug. 2013, each of which are incorporated in their entirety by this reference, and/or can be performed in any suitable manner.

4. System

Figure 5:
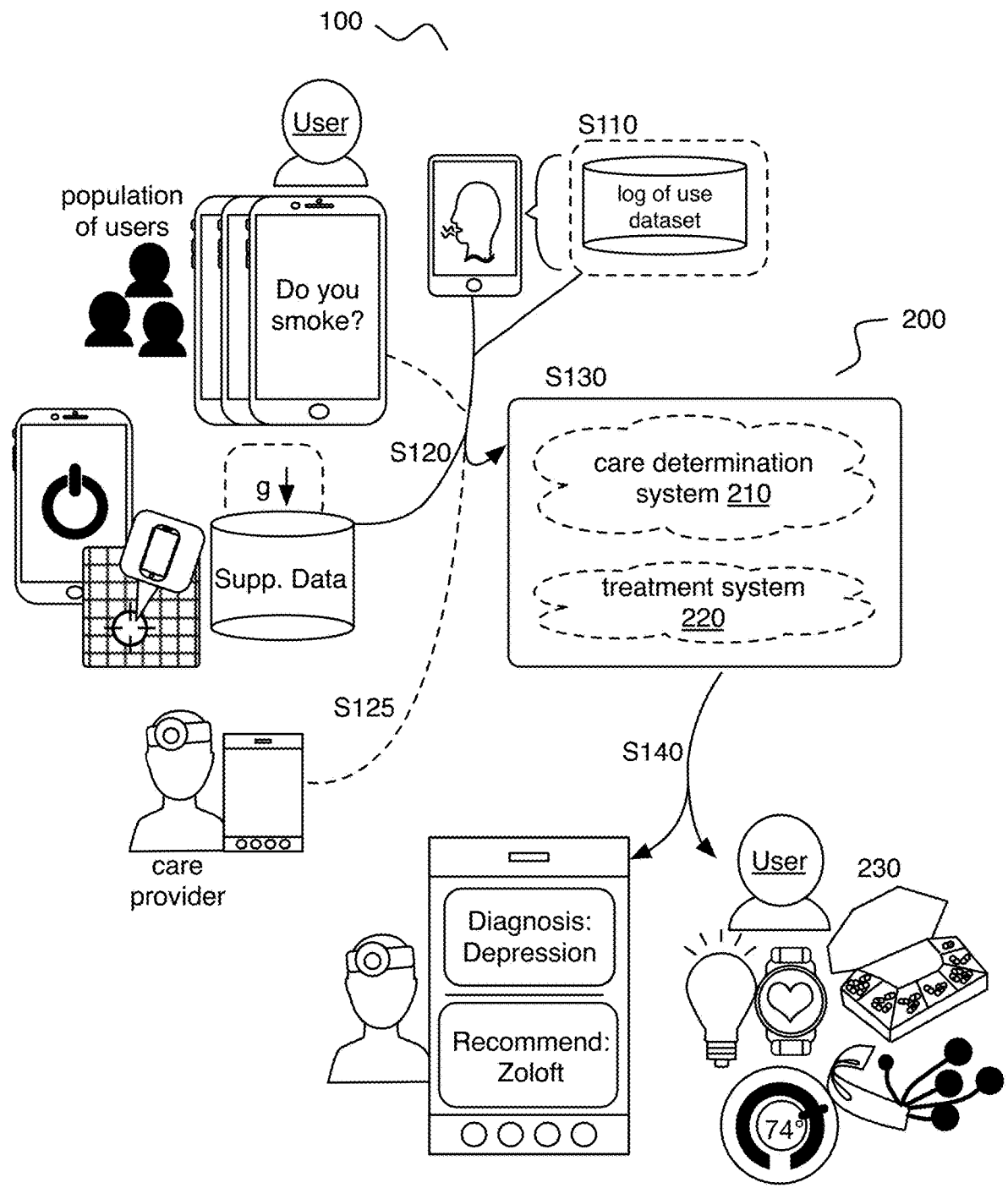
FIG. 5 is a schematic representation of variations of a system.
Figure 6A:
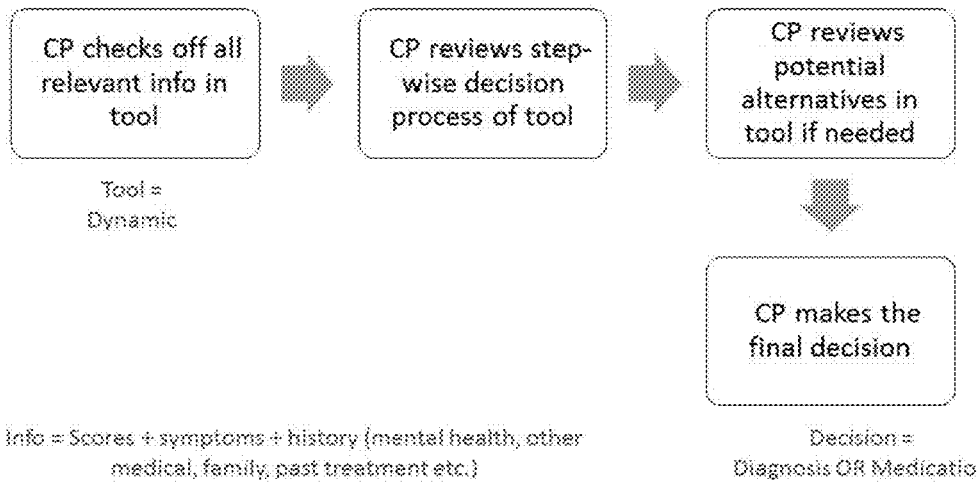
FIGS. 6A-6B, 7, 8, 9A-9B are examples of patient and/or care provider experiences in variations of a method.
Figure 6B:
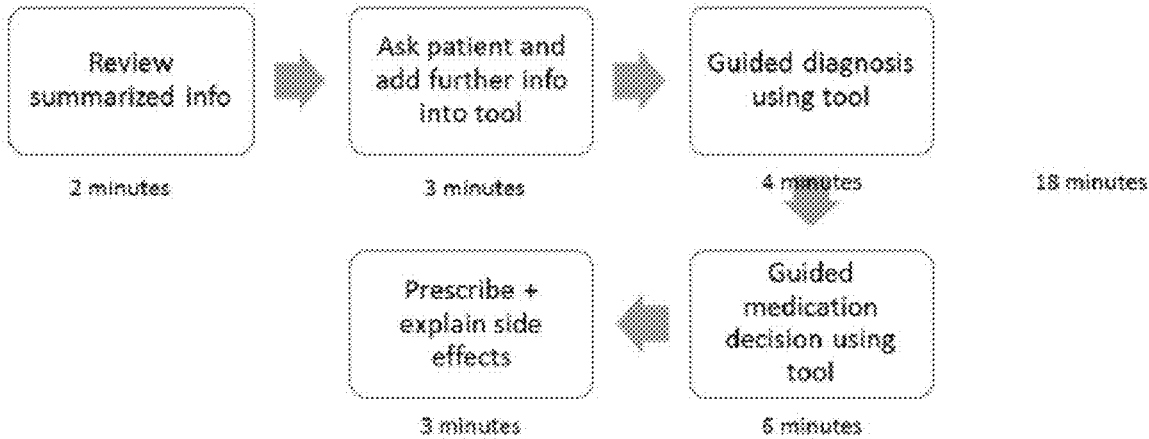
Figure 7:
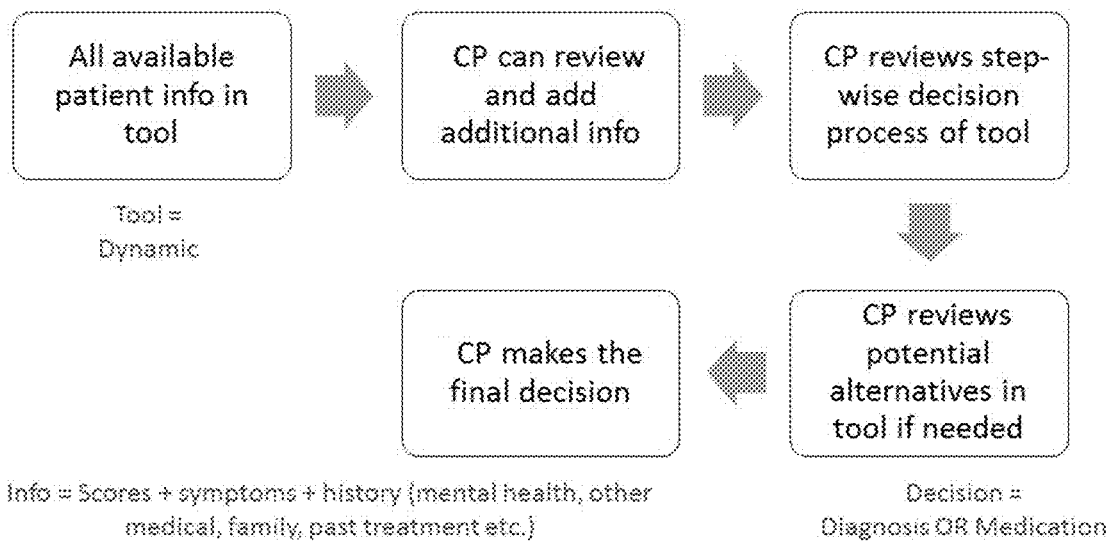
Figure 8:
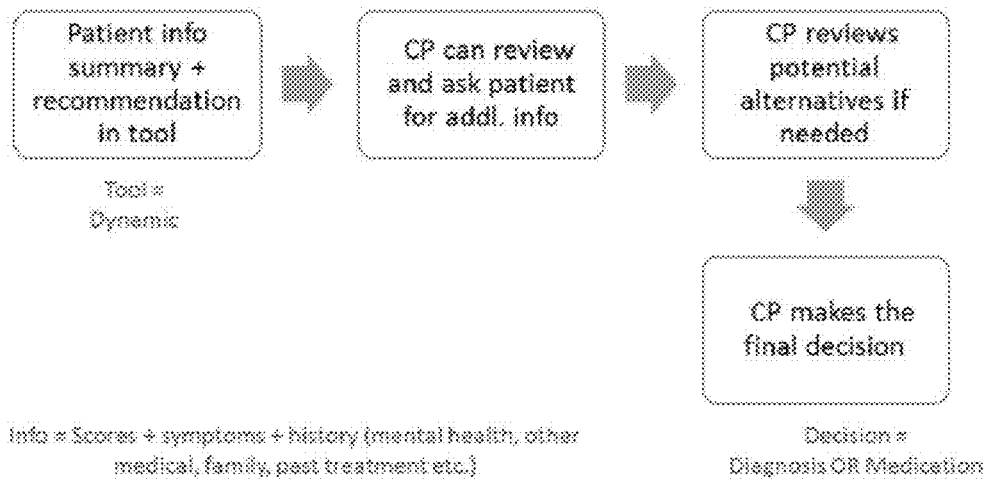
Figure 9A:
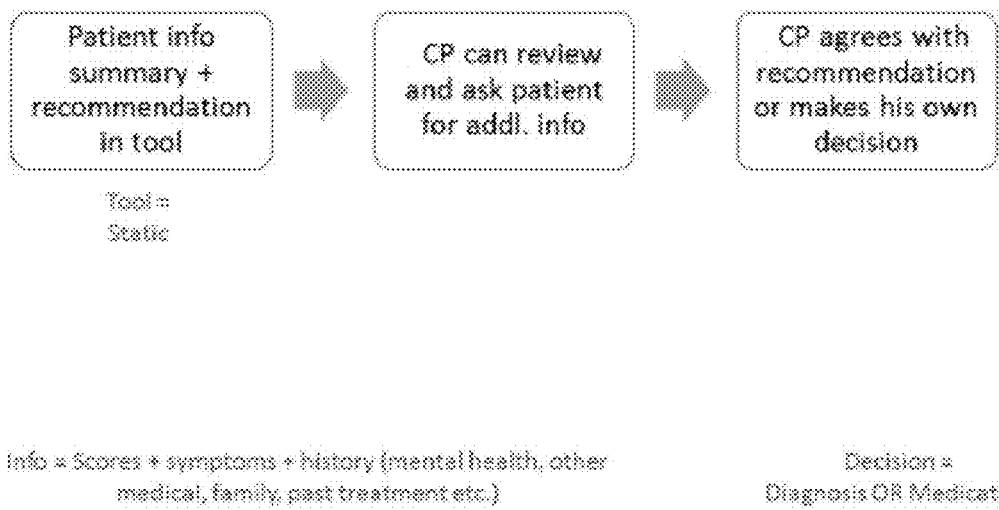
Figure 9B:
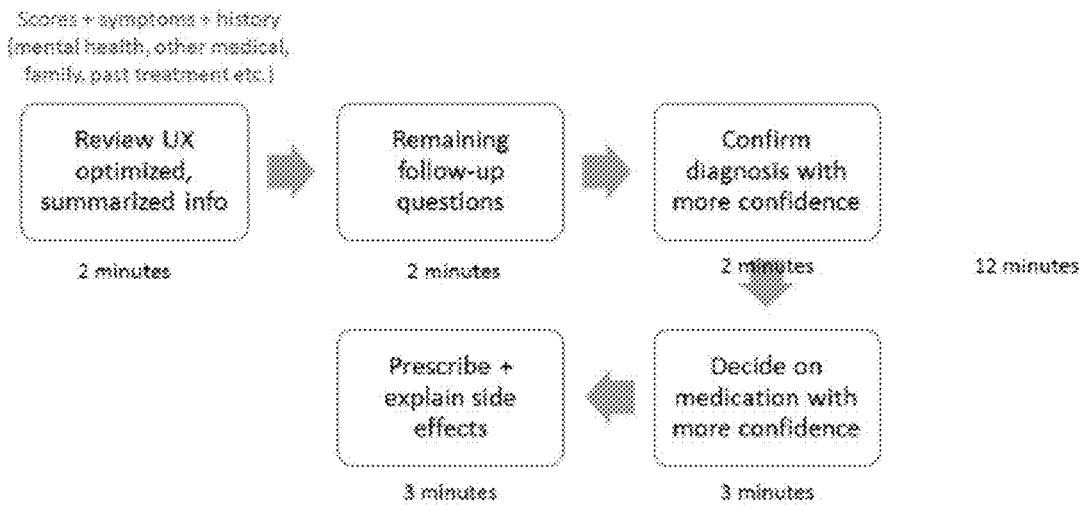

As shown in FIG. 5, embodiments of a system 200 for improving care determination in relation to a condition of a user associated with a mobile device can include a care determination system 210 operable to perform Blocks S110-S150 and/or other portions of the method 100; and a treatment system 220 operable to automatically promote a medical status analysis (e.g., to a care provider) associated with the condition and/or user. The care determination system 210 and/or treatment system 220 can include a processing system, an interface operable to present medical status analyses; and/or any other suitable components operable to perform any suitable portions of the method 100. The system 200 can additionally or alternatively include a supplemental device 230 (e.g., a supplemental medical device, a supplemental personal assistant device, etc.) and/or any other suitable components. While the components of the system 200 are generally described as distinct components, they can be physically and/or logically integrated in any manner. For example, a remote computing system can implement functionality associated with both the care determination system 210 and treatment system 220. In another example, functionality can be shared between the care determination system 210, the treatment system 220, and/or any other suitable components of the system 200. The system 200 and/or components of the system 200 (e.g., care determination system 210, treatment system 220, etc.) can entirely or partially be executed by, hosted on, communicate with, and/or otherwise include: user databases (e.g., storing patient characteristics, user health records, associated care provider characteristics, patient device information, etc.), analysis databases (e.g., storing computational models, collected datasets, features, rules, medical status analyses, etc.), remote computing systems, user devices, care provider devices, and/or any other suitable components. Additionally or alternatively, the components of the system can be distributed across machine and cloud-based computing systems in any other suitable manner. However, the system 200 and associated components can be configured in any manner analogous to U.S. application Ser. No. 15/482,995 filed 10 Apr. 2017, U.S. application Ser. No. 13/969,339 entitled "Method for Modeling Behavior and Health Changes" and filed on 16 Aug. 2013, U.S. application Ser. No. 15/265,454 entitled "Method for Providing Health Therapeutic Interventions to a User" and filed on 14 Sep. 2016, and U.S. application Ser. No. 15/245,571 entitled "Method and System for Modeling Behavior and Heart Disease State" and filed on 24 Aug. 2016, each of which are herein incorporated in their entirety by this reference, and/or can be configured in any suitable manner.

The care determination system 210 functions to collect and process datasets (e.g., described in Blocks S110-S125) in determining medical status analyses. For example, the care determination system 210 can obtain, apply, and/or otherwise manipulate computer-implemented rules (e.g., feature engineering rules) in deriving features for and/or otherwise generating medical status analyses. In a specific example, the care determination system 210 can receive mobility supplementary data corresponding to mobility-related sensors including GPS receivers operable to collect GPS satellite data during the time period; extract features (e.g., with a remote central processing unit) based on the GPS satellite data, the features operable to improve determination of medical status analyses; and generate a medical status analysis associated with the location of the GPS receiver (e.g., during a time period in which a log of use dataset and/or other suitable datasets were collected, etc.), based on the features. In another specific example, the care determination system 210 can receive mobility supplementary data including an orientation of the mobile device (e.g., during a time period), the orientation determined based on signals from a set of inertial sensors mounted respectively at the mobile device; and extract features (e.g., mobility-communication features) based on the orientation. However, the care determination system 210 can be configured in any suitable manner.

The treatment system 220 functions to promote medical status analyses (e.g., in a manner analogous to Block S140, etc.) to care providers, users, and/or any other suitable entities. The treatment system 220 can include any one or more of supplementary medical devices 230 (e.g., ambient environment devices such as sensing and control systems for temperature, light, air quality and/or composition, humidity; biometric devices such as cardiovascular, EEG, EOG, EMG, ECG; medication devices such as automatic medication dispensers; personal assistant devices; etc.), mobile devices (e.g., mobile communication devices from which a log of use dataset is collected; user devices; care provider devices; etc.), and/or any other suitable devices. In an example, the treatment system 220 can be operable to generate, transmit, and/or apply control instructions for operating a supplemental device 230 and/or other suitable device (e.g., a medical device of the treatment system 220) to promote the medical status analyses (e.g., controlling a user device administer a guided meditation to the user, etc.). In another example, the treatment system 220 can be operable to automatically initiate a signal that controls an automated medication system (e.g., a signal for updating medication regimen parameters such as schedule, dosage, medication type, etc.; a signal activating the automated medication system to alert the user in relation to a medication regimen; etc.). However, the treatment system 220 can be configured in any suitable manner.

An alternative embodiment preferably implements the above methods in a computer-readable medium storing computer-readable instructions. The instructions are preferably executed by computer-executable components preferably integrated with a user interface configuration system. The computer-readable medium may be stored on any suitable computer readable media such as RAMs, ROMs, flash memory, EEPROMs, optical devices (CD or DVD), hard drives, floppy drives, or any suitable device. The computer-executable component is preferably a processor but the instructions may alternatively or additionally be executed by any suitable dedicated hardware device. Although omitted for conciseness, the preferred embodiments include every combination and permutation of the various system components and the various method processes.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. As a person skilled in the art will recognize from the previous detailed description and from the figures and claims, modifications and changes can be made to the preferred embodiments of the invention without departing from the scope of this invention defined in the following claims.

We claim:

1. A system for improving care determination in relation to a condition of a user associated with a user mobile device, the system comprising:
   a care determination system communicatively coupled to the user mobile device, a care professional mobile device of a care professional of the user, and a treatment system, the care determination system being operable to:
   collect, from the user mobile device, log of use data associated with user digital communications at the user mobile device during a time period;
   collect, from the user mobile device, mobility sensor supplementary data sampled at a mobility-related sensor of the user mobile device during the time period, the mobility sensor supplementary data being associated with a mobility behavior for the user of the user mobile device;
   extract, from the log of use data and the mobility sensor supplementary data collected from the user mobile device, mobility-communication features associated with the time period based on a first feature engineering rule operable to improve the care determination system;
   collect care professional data from the care professional mobile device via a network, the care professional data associated with the condition and the time period;
   determine a care status analysis of the user for the condition of the user based on the extracted mobility-communication features and the collected care professional data, wherein the care status analysis comprises a treatment for improving the condition;
   provide the care status analysis of the user to the treatment system;
   the treatment system, wherein the treatment system is constructed to automatically provide at least a portion of the care status analysis of the user to the care professional mobile device, in response to the care status analysis received from the care determination system;
   the care professional mobile device, wherein the care professional mobile device is constructed to automatically display information identifying the treatment comprising a medication for improving the condition of the user, wherein the displayed information is used by the care professional to administer the treatment to the user; and
   an automated medication system, wherein the treatment system automatically initiates a signal that controls the automated medical system to dispense the medication for improving the condition, wherein the medication system dispenses the medication in response to the signal.

2. The system of claim 1,
wherein the care determination system is further operable to:
   determine a reasoning component of the care status analysis based on the condition, the reasoning component associated with determination of the treatment; and
   modify a visually perceptible digital element of the care status analysis based on the condition, the visually perceptible digital element associated with the reasoning component and operable to improve display of the care status analysis; and
wherein the treatment system is operable to automatically present the reasoning component and the treatment to the care professional mobile device for improving the condition.

3. The system of claim 1,
wherein the mobility-related sensor comprises a GPS receiver operable to collect GPS satellite data during the time period,
wherein the care determination system comprises a remote central processing unit (CPU) operable to extract the mobility-communication features using the GPS satellite data, wherein the mobility-communication features are operable to improve determination of the care status analysis by the remote CPU, and wherein the care status analysis is associated with the location of the GPS receiver during the time period, and
wherein the treatment system is operable to control the care professional mobile device to present the care status analysis comprising the treatment.

4. The system of claim 1,
wherein the mobility sensor supplementary data comprises an orientation of the user mobile device during the time period, the orientation determined based on signals from a set of inertial sensors mounted respectively at the user mobile device during the time period; and
wherein the care determination system is operable to extract the mobility-communication features based on the orientation.

5. The system of claim 1, wherein the care determination system is further operable to:
   obtain the first feature engineering rule defining the care status analysis as a function of the log of use data and the mobility sensor supplementary data; and
   generate the mobility-communication features based on evaluating the log of use data and the mobility sensor supplementary data against the first feature engineering rule.

6. The system of claim 5, wherein the care determination system is further operable to:
   obtain a second feature engineering rule operable to associate the mobility-communication features with the care professional data, wherein the second feature engineering rule is further operable to improve the care determination system;
   modify the mobility-communication features based on the care professional data; and
   determine the care status analysis based on the modified mobility-communication features.

7. The system of claim 1,
wherein the care determination system is operable to determine the medication based on the mobility-communication features and the care professional data.

8. The system of claim 1, wherein the care determination system is operable to:
assign the user to a user subgroup of a set of user subgroups, based on the mobility-communication features and the care professional data, wherein the user subgroup shares a mobility-communication behavior and is operable to improve care determination for the condition; and
determine the care status analysis based on the user subgroup, the mobility-communication features, and the care professional data.

9. A method for improving care determination in relation to a condition of a first user associated with a first user mobile device, the method comprising:
collecting, from the first user mobile device, a first log of use dataset associated with first user digital communication behavior at the first user mobile device;
collecting, from the first user mobile device, a first mobility sensor supplementary dataset corresponding to a first mobility-related sensor of the first user mobile device;
determining a medical status analysis for the first user based on the first log of use dataset and the first mobility sensor supplementary dataset, the medical status analysis comprising a diagnosis and a therapeutic intervention associated with the condition;
promoting the diagnosis and the therapeutic intervention from the medical status analysis for improving the care determination by communicating with a first care provider mobile device of a first care provider of the first user;
collecting a first care provider dataset from the first care provider mobile device, wherein the first care provider dataset is associated with the medical status analysis;
updating the medical status analysis for the condition based on the first care provider dataset; and
administering at least one therapeutic intervention to the first user based on the updated medical status analysis.

10. The method of claim 9,
wherein the first care provider dataset comprises user-first care provider interaction data between the first user and the first care provider, and the method further comprising:
collecting a second care provider dataset from a second care provider mobile device, the second care provider dataset comprising user-second care provider interaction data between the first user and the second care provider,
wherein updating the medical status analysis comprises updating the medical status analysis based on the user-first care provider interaction data and the user-second care provider interaction data.

11. The method of claim 10, further comprising collecting first care provider-second care provider interaction data between the first and the second care providers, wherein updating the medical status analysis comprises updating the medical status analysis based on the first care provider-second care provider interaction data, the user-first care provider interaction data, and the user-second care provider interaction data.

12. The method of claim 11, wherein collecting the first care provider-second care provider interaction data comprises:
automatically initiating, during a user-first care provider interaction period associated with the user-first care provider interaction data, a telemedicine communication through a wireless communicable link between the first care provider mobile device, associated with the first care provider, and the second care provider device, associated with the second care provider; and
collecting the first care provider-second care provider interaction data based on the telemedicine communication.

13. The method of claim 9,
wherein determining the medical status analysis comprises:
determining the diagnosis with a diagnosis model based on the first log of use dataset and the first mobility sensor supplementary dataset; and
determining the therapeutic intervention with a therapeutic intervention model based on the diagnosis; and
wherein updating the medical status analysis comprises:
updating the diagnosis and the therapeutic interventions based on the diagnosis model, the therapeutic intervention model, and the first care provider dataset.

14. The method of claim 13,
wherein collecting the first care provider dataset comprises collecting the first care provider dataset during a user-care provider interaction period, and
wherein updating the medical status analysis comprises, in response to collecting the first care provider dataset:
retrieving the diagnosis model during the user-care provider interaction period;
retrieving the therapeutic intervention model during the user-care provider interaction period; and
updating the medical status analysis in real-time during the user-care provider interaction period based on the diagnosis model, the therapeutic intervention model, and the first care provider dataset.

15. The method of claim 9,
wherein the first log of use dataset and the first mobility sensor supplementary dataset are associated with a first time period, and the method further comprising:
collecting a second log of use dataset associated with the user digital communication behavior at the first user mobile device during a second time period subsequent the first time period; and
collecting a second mobility sensor supplementary dataset corresponding to the mobility-related sensor of the first user mobile device during the second time period,
wherein updating the medical status analysis comprises updating the medical status analysis based on the second log of use dataset, the second mobility sensor supplementary dataset, and the first care provider dataset.

16. The method of claim 15, wherein determining the medical status analysis comprises determining a medication dosage for the condition based on the first log of use dataset and the first mobility sensor supplementary dataset, and wherein updating the medical status analysis comprises updating the medication dosage based on the second log of use dataset, the second mobility sensor supplementary dataset, and the first care provider dataset.

17. The method of claim 15, further comprising:
collecting an additional log of use data corresponding to second user digital communication behavior at a second user mobile device associated with a second user; and collecting an additional mobility sensor supplementary dataset corresponding to a second mobility-related sensor of the second user mobile device;

wherein updating the medical status analysis comprises updating the medical status analysis based on the additional log of use data, the additional mobility sensor supplementary dataset, the second log of use dataset, the second mobility sensor supplementary dataset, and the first care provider dataset.

18. The method of claim 17, wherein the first care provider dataset comprises first user-care provider interaction data between the first user and the first care provider, and the method further comprising:

collecting a second care provider dataset comprising second user-care provider interaction data between the second user and the first care provider, wherein the first user-care provider interaction data and the second user-care provider interaction data are associated with the condition, wherein updating the medical status analysis comprises updating the medical status analysis based on the first and the second care provider datasets, the additional log of use data, the additional mobility sensor supplementary dataset, the second log of use dataset, and the second mobility sensor supplementary dataset.

19. The method of claim 9, further comprising:

determining a medical status generation frequency based on the diagnosis associated with the condition, wherein updating the medical status analysis comprises updating the medical status analysis based on the medical status generation frequency and the first care provider dataset.

20. The method of claim 9, further comprising:

determining effectiveness of the therapeutic intervention;

in response to the effectiveness being below a threshold condition, determining a match between the first user and a second care provider based on the first log of use dataset, the first mobility sensor supplementary dataset, and the diagnosis; and presenting the match to the first care provider.

* * * * *